US008337824B2

(12) United States Patent
Albrecht et al.

(10) Patent No.: US 8,337,824 B2
(45) Date of Patent: Dec. 25, 2012

(54) LINEAR POLYOL STABILIZED POLYFLUOROACRYLATE COMPOSITIONS

(75) Inventors: Detlef Albrecht, Saratoga, CA (US);
Michael Burdick, Los Altos, CA (US);
Han-Ting Chang, Livermore, CA (US);
Dominique Charmot, Campbell, CA (US); Ramakrishnan Chidambaram, Pleasanton, CA (US); Eric Connor, Los Gatos, CA (US); Sherin Halfon, Palo Alto, CA (US); I-Zu Huang, Mountain View, CA (US); Mingjun Liu, Campbell, CA (US); Jonathan Mills, San Jose, CA (US); Werner Strüver, Leverkusen (DE)

(73) Assignee: Relypsa, Inc., Santa Clara, CA (US)

( * ) Notice: Subject to any disclaimer, the term of this patent is extended or adjusted under 35 U.S.C. 154(b) by 278 days.

(21) Appl. No.: 12/545,810

(22) Filed: Aug. 22, 2009

(65) Prior Publication Data
US 2010/0111891 A1    May 6, 2010

Related U.S. Application Data

(60) Provisional application No. 61/165,899, filed on Apr. 1, 2009, provisional application No. 61/091,097, filed on Aug. 22, 2008.

(51) Int. Cl.
*A61K 47/10* (2006.01)
*A61K 31/75* (2006.01)
*A61K 31/755* (2006.01)
*A61K 31/785* (2006.01)
*A61K 31/047* (2006.01)
*C08F 220/22* (2006.01)
*C08F 220/04* (2006.01)
*C08F 299/00* (2006.01)
*C08F 236/00* (2006.01)
*C08F 236/20* (2006.01)
*C08F 230/02* (2006.01)

(52) U.S. Cl. ...... 424/78.1; 526/72; 526/245; 526/292.1; 526/292.95; 526/292.7; 526/292.6; 526/309; 526/310; 526/318; 526/318.1; 526/319; 526/326; 526/328; 526/334; 526/336; 526/337; 526/340; 526/340.2; 526/340.3; 526/346; 526/347; 526/347.1; 514/724; 514/75; 514/579; 514/722; 514/743

(58) Field of Classification Search .................. None
See application file for complete search history.

(56) References Cited

U.S. PATENT DOCUMENTS

| | | | |
|---|---|---|---|
| 2,611,730 | A | 9/1952 | Heming |
| 2,909,462 | A | 10/1959 | Warfield et al. |
| 3,499,960 | A | 3/1970 | Macek et al. |
| 3,874,907 | A | 4/1975 | Gardon et al. |
| 3,974,272 | A | 8/1976 | Polli et al. |
| 4,143,130 | A | 3/1979 | Imondi et al. |
| 4,470,975 | A | 9/1984 | Berger et al. |
| 4,492,205 | A | 1/1985 | Jundt et al. |
| 4,605,701 | A | 8/1986 | Harada et al. |
| 4,747,881 | A | 5/1988 | Shaw et al. |
| 4,837,015 | A | 6/1989 | Olsen |
| 4,902,501 | A | 2/1990 | Bandi et al. |
| 4,942,205 | A | 7/1990 | Ohmori et al. |
| 5,051,253 | A | 9/1991 | Lloyd-Jones et al. |
| 5,091,175 | A | 2/1992 | Imondi et al. |
| 5,141,927 | A | 8/1992 | Krotkiewski |
| 5,186,937 | A | 2/1993 | Sparks et al. |
| 5,281,631 | A | 1/1994 | Horwitz et al. |
| 5,374,422 | A | 12/1994 | St. Pierre et al. |
| 5,413,782 | A | 5/1995 | Warchol et al. |
| 5,487,888 | A | 1/1996 | Mandeville, III et al. |
| 5,607,669 | A | 3/1997 | Mandeville, III et al. |
| 5,618,530 | A | 4/1997 | Mandeville, III et al. |
| 5,633,344 | A | 5/1997 | Figuly |
| 5,667,775 | A | 9/1997 | Holmes-Farley et al. |
| 5,679,717 | A | 10/1997 | Mandeville, III et al. |
| 5,693,675 | A | 12/1997 | Mandeville, III et al. |
| 5,702,696 | A | 12/1997 | Mandeville, III et al. |
| 5,718,920 | A | 2/1998 | Notenbomer |
| 5,846,990 | A | 12/1998 | Murugesan et al. |
| 5,935,599 | A | 8/1999 | Dadey |
| 6,280,717 | B1 | 8/2001 | Kamakura et al. |
| 6,294,163 | B1 | 9/2001 | Dhal et al. |
| 6,881,484 | B2 | 4/2005 | Kataoka et al. |
| 7,429,394 | B2 | 9/2008 | Charmot et al. |
| 7,488,495 | B2 | 2/2009 | Charmot et al. |
| 7,556,799 | B2 | 7/2009 | Charmot et al. |
| 2002/0054903 | A1 | 5/2002 | Tyler et al. |

(Continued)

FOREIGN PATENT DOCUMENTS

EP    0730494 A1    9/1996

(Continued)

OTHER PUBLICATIONS

Rideaux (American Nuclear Society Third Topical Meeting DOE Spend Nuclear Fuel and Fissile Materials Management, Charleston, SC (USA), Sep. 8-11, 1998, Published Mar. 8, 1999, pp. 1-10).*
Agarwal, R., et al., "Pathophysiology of Potassium Absorption and Secretion by the Human Intestine," Gastroenterology, 1994, pp. 548-571, vol. 107, American Gastroenterological Association.
Arshady, R., "Biodegradable Microcapsular Drug Delivery Systems: Manufacturing Methodology, Release Control and Targeting Prospects," Journal of Bioactive and Compatible Polymers, Jul. 1990, pp. 315-342, vol. 5.
Berlyne, G. M., et al., "Cation Exchange Resins in Hyperkalaemic Renal Failure," Israel J. Med Sci., 1967, pp. 45-52, vol. 3, No. 1.

(Continued)

*Primary Examiner* — Richard Schnizer
*Assistant Examiner* — Alma Pipic
(74) *Attorney, Agent, or Firm* — Senniger Powers LLP

(57) ABSTRACT

The present invention is directed to compositions of a linear polyol and a salt of a crosslinked cation exchange polymer comprising a fluoro group and an acid group. These compositions are useful to bind potassium in the gastrointestinal tract.

78 Claims, No Drawings

U.S. PATENT DOCUMENTS

| | | | |
|---|---|---|---|
| 2002/0054913 | A1 | 5/2002 | Heese et al. |
| 2002/0146386 | A1 | 10/2002 | Simon et al. |
| 2003/0027789 | A1 | 2/2003 | Yamaoka et al. |
| 2003/0065090 | A1 | 4/2003 | Kelly et al. |
| 2004/0166156 | A1 | 8/2004 | Tyler et al. |
| 2004/0251204 | A1 | 12/2004 | Paananen et al. |
| 2005/0036983 | A1 | 2/2005 | Simon et al. |
| 2005/0220750 | A1 | 10/2005 | Robert et al. |
| 2005/0220751 | A1 | 10/2005 | Charmot et al. |
| 2005/0220752 | A1 | 10/2005 | Charmot et al. |
| 2005/0220889 | A1 | 10/2005 | Charmot et al. |
| 2005/0220890 | A1 | 10/2005 | Charmot et al. |
| 2006/0024265 | A1 | 2/2006 | Alpern et al. |
| 2006/0024336 | A1 | 2/2006 | Charmot et al. |
| 2007/0059277 | A1 | 3/2007 | Bhagat et al. |
| 2008/0233073 | A1 | 9/2008 | Charmot et al. |
| 2008/0241092 | A1 | 10/2008 | Charmot et al. |
| 2008/0241093 | A1 | 10/2008 | Charmot et al. |
| 2008/0260679 | A1 | 10/2008 | Charmot et al. |
| 2009/0148533 | A1 | 6/2009 | Charmot et al. |
| 2009/0155370 | A1 | 6/2009 | Cope et al. |
| 2009/0186093 | A1 | 7/2009 | Liu et al. |
| 2010/0104527 | A1 | 4/2010 | Mansky et al. |
| 2010/0111892 | A1 | 5/2010 | Chang et al. |

FOREIGN PATENT DOCUMENTS

| | | | |
|---|---|---|---|
| EP | 1 785 141 A1 | | 5/2007 |
| JP | 1998-059851 A | | 3/1998 |
| JP | 1998-130154 A | | 5/1998 |
| JP | 2004-149525 A | | 5/2004 |
| WO | 82/00257 A1 | | 2/1982 |
| WO | 92/10522 A1 | | 6/1992 |
| WO | 94/27619 A1 | | 12/1994 |
| WO | 95/14531 A1 | | 6/1995 |
| WO | 97/49387 A1 | | 12/1997 |
| WO | 97/49736 A2 | | 12/1997 |
| WO | 00/40224 A1 | | 7/2000 |
| WO | 01/51063 A1 | | 7/2001 |
| WO | 02/12160 A1 | | 2/2002 |
| WO | 02/40039 A2 | | 5/2002 |
| WO | 02/062356 A2 | | 8/2002 |
| WO | 2005/065291 A2 | | 7/2005 |
| WO | 2007/038801 A1 | | 4/2007 |
| WO | 2007/038802 A2 | | 4/2007 |
| WO | 2007/041569 A1 | | 4/2007 |
| WO | WO 2007/038802 A2 | * | 4/2007 |
| WO | 2009/029830 A1 | | 3/2009 |
| WO | 2010/022381 A1 | | 2/2010 |
| WO | 2010/022382 A2 | | 2/2010 |
| WO | 2010/022383 A2 | | 2/2010 |

OTHER PUBLICATIONS

Blake, J., et al., "Differential Effects of Direct Antagonism of All Compared to ACE Inhibitors on Serum Potassium Levels and Azotemia in Patients with Severe Congestive Heart Failure," Congestive Heart Failure, Jul./Aug. 2000, pp. 193-196, vol. 6, No. 4, CHF, Inc., Darien, Connecticut.

Chourasia, M. K., et al., "Pharmaceutical Approaches to Colon Targeted Drug Delivery Systems," J. Pharm Pharm Sci., 2003, pp. 33-66, vol. 6, No. 1.

Coli, L., et al., "Phosphate Removal by Resin Hemoperfusion Efficacy and Biocompatibility of a New Exchange Resin," Biomaterials, Artificial Cells, and Immobilization Biotechnology, 1992, pp. 1153-1163, vol. 20, No. 5.

Corcoran, A. C., et al., "Controlled Observations on the Effect of Low Sodium Dietotherapy in Essential Hypertension," Circulation, The Journal of the American Heart Association, Jan. 1951, pp. 1-16, vol. 3, No. 1.

Cuña, M. et al., "Controlled-Release Liquid Suspensions Based on Ion-Exchange Particles Entrapped Within Acrylic Microcapsules," International Journal of Pharmaceutics, 2000, pp. 151-158, vol. 199, Elsevier Science.

Dai, J., et al., "Controlling Ion Transport through Multilayer Polyelectrolyte Membranes by Derivatization with Photolabile Functional Groups," Macromolecules, 2002, pp. 3164-3170, vol. 35, American Chemical Society.

Danowski, T. S., et al., "Changes in Fecal and Serum Constituents During Ingestion of Cation and Anion Exchangers," Annals New York Academy Sciences, 1953, pp. 273-279, vol. 57, No. 3.

Emerson, Jr., K., et al., "The Role of the Gastro-Intestinal Tract in the Adaptation of the Body to the Prevention of Sodium Depletion by Cation Exchange Resins," Annals New York Academy Sciences, 1953, pp. 280-290, vol. 57, No. 3.

Emmett, M., et al., "Effect of Three Laxatives and a Cation Exchange Resin on Fecal Sodium and Potassium Excretion," Gastroenterology, 1995, pp. 752-760, vol. 108, No. 3.

Estrela-Lopis, I., et al., "SANS Studies of Polyelectrolyte Multilayers on Colloidal Templates", Langmuir, 2002, pp. 7861-7866, vol. 18, American Chemical Society.

Evans, B. M., et al., "Ion-Exchange Resins in the Treatment of Anuria," Lancet, Oct. 17, 1953, pp. 791-795, vol. 265, No. 6790.

Field, Jr., H., et al., "Electrolyte Changes in Ileal Contents and in Feces During Restriction of Dietary Sodium With and Without the Administration of Cation-Exchange Resin," Circulation, Oct. 1955, pp. 625-629, vol. 12, No. 4.

Field, Jr., H., et al., "Mechanisms Regulating the Retention of Sodium in the Feces by Cation-Exchange Resin: Release of Base from the Resin by Bacterial Fermentation in the Terminal Ileum," J. Lab. & Clin. Med., Feb. 1958, pp. 178-184, vol. 51, No. 2.

Forrest, M. L., et al., "A Degradable Polyethylenimine Derivative with Low Toxicity for Highly Efficient Gene Delivery," Bioconjugate Chem., 2003, pp. 934-940, vol. 14, No. 5.

Fourman, P., "Capacity of a Cationic Exchange Resin (zeo-karb 225) In Vivo," British Medical Journal, Mar. 7, 1953, pp. 544-546, vol. 1, No. 4809.

Friedman, E. A., "Sorbent Therapy in Uremia," Chapter 24, Clinical Aspects of Uremia and Dialysis, 1976, pp. 671-687.

Friedman, E. A., et al., "Combined Oxystarch-Charcoal Trial in Uremia: Sorbent-induced Reduction in Serum Cholesterol," Kidney International, 1976, pp. S273-S276, vol. 10.

Gerstman, B. B., et al., "Use of Sodium Polystyrene Sulfonate in Sorbitol in The United States," American Journal of Kidney Diseases, Nov. 1991, pp. 619-621, vol. XVIII, No. 5.

Greenman, L., et al., "Biochemical Changes Accompanying the Ingestion of a Carboxylic Cation Exchanger in the Hydrogen, Ammonium, Sodium, Potassium, or Calcium Form", J. Clin. Invest., 1951, pp. 995-1008, vol. 30, No. 9.

Gruy-Kapral, C., et al., "Effect of Single Dose Resin-Cathartic Therapy on Serum Potassium Concentration in Patients With End-Stage Renal Disease," J. Am. Soc. Nephrol., 1998, pp. 1924-1930, vol. 9, No. 10.

Harthon, J. G. L., et al., "A Case of Uremia and Hyperpotassemia Treated With Sulphonic Cation-Exchange Resin," Acta Medica Scandinavica, 1952, pp. 230-236, vol. 144, No. 3.

Heming, A. E., et al., "Considerations in the Selection of Cation Exchange Resins for Therapeutic Use", Annals New York Academy of Sciences, 1953, pp. 239-251, vol. 57, No. 3.

Ichikawa, H. et al., "Use of Ion-Exchange Resins to Prepare 100 µm-sized Microcapsules with Prolonged Drug-Release by the Wurster Process," International Journal of Pharmaceutics, 2001, pp. 67-76, vol. 216, Elsevier Science.

Imondi, A. R., et al., "Gastrointestinal Sorbents for the Treatment of Uremia I. Lightly Cross-Linked Carboxyvinyl Polymers," Ann. Nutr. Metabol., 1981, pp. 311-319, vol. 25, No. 5.

Irwin, L., et al., "The Effect of a Cation Exchange Resin on Electrolyte Balance and Its Use in Edematous States," J. Clin. Invest., 1949, pp. 1403-1411, vol. 28, No. 6, Part 2.

Johnson, K., et al., "Sodium Polystyrene Sulfonate Resin Candy for Control of Potassium in Chronic Dialysis Patients," Clinical Nephrology, 1976, pp. 266-268, vol. 5, No. 6.

Kim, H.-J. et al "Therapeutic Approach to Hyperkalemia," Nephron, 2002, pp. 33-40, vol. 92, Supplement 1, Division of Nephrology, Department of Internal Medicine, Hanyang University Kuri Hospital, Kuri, Korea.

Kohlstaedt, K. G., et al., "Clinical Experience With Mixtures of Anion and Cation Exchange Resins," Annals New York Academy of Sciences, 1953, pp. 260-272, vol. 57, No. 3.

Koping-Hoggard, M., et al., "Chitosan as a Nonviral Gene Delivery System. Structure-Property Relationships and Characteristics Compared with Polyethylenimine In Vitro and After Lung Administration In Vivo," Gene Therapy, 2001, pp. 1108-1121, vol. 8.

Mason, N. S., et al., "A New Ion Exchanger With High In Vivo Sodium Capacity," Kidney International, 1985, pp. S178-S182, vol. 28, Supplement 17.

Mateer, F. M., et al., "Sodium Restriction and Cation Exchange Resin Therapy in Nephrotic Children," J. Clin. Invest., 1951, pp. 1018-1026, vol. 30, No. 9.

McChesney, E.W., "Effects of Long-Term Feeding of Sulfonic Ion Exchange Resin on the Growth and Mineral Metabolism of Rats," Am. J. Physiol., Jun. 1954, pp. 395-400, vol. 177, No. 3.

McChesney, E. W., et al., "Some Aspects of Cation Exchange Resins as Therapeutic Agents for Sodium Removal," Annals New York Academy of Sciences, 1953, pp. 252-259, vol. 57, No. 3.

Meszaros, R., et al., "Adsorption of Poly(ethyleneimine) on Silica Surfaces: Effect of pH on the Reversibility of Adsorption," Langmuir, 2004, pp. 5026-5029, vol. 20, American Chemical Society.

Moustafine, R. I., et al., "Characteristics of Interpolyelectrolyte Complexes of Eudragit E 100 With Sodium Alginate", International Journal of Pharmaceutics, 2005, pp. 113-120, vol. 294, Nos. 1-2.

Picart, C., et al., "Microinterferometric Study of the Structure, Interfacial Potential, and Viscoelastic Properties of Polyelectrolyte Multilayer Films on a Planar Substrate," J. Phys. Chem. B, 2004, pp. 7196-7205, vol. 108, American Chemical Society.

Root, M. A., "Comparison of the In Vivo Sodium-Removing Activity of Various Types of Ion Exchange Resins in Rats," J. Lab. Clin. Med., 1953, pp. 430-437, vol. 42, No. 3.

Ross, E. J., et al., "Observations on Cation Exchange Resins in the Small and Large Intestines," 1954, pp. 555-566, Medical Unit, University College Hospital Medical School, London, W.C.1.

Salas-Coll, C. A., et al., "Potassium Transport Across the Distal Colon in Man," Clinical Science and Molecular Medicine, 1976, pp. 287-296, vol. 51.

Spencer, A. G., et al., "Cation Exchange in the Gastrointestinal Tract," British Medical Journal, Mar. 13, 1954, pp. 603-606.

Thies, C., "Microcapsules as Drug Delivery Devices," CRC Critical Reviews in Biomedical Engineering, 1982, pp. 335-383, vol. 8, No. 4.

Thomas, M., et al., "Cross-Linked Small Polyethylenimines: While Still Nontoxic, Deliver DNA Efficiently to Mammalian Cells In Vitro and In Vivo," Pharmaceutical Research, Mar. 2005, pp. 373-380, vol. 22, No. 3.

Tust, R. H., et al., "The Effects of Malethamer on the Excretion and Plasma Levels of Sodium, Potassium, and Chloride (34990)," Proc. Soc. Exp. Biol. Med., 1970, pp. 72-76, vol. 135, No. 1.

Wrong, O., et al., "The Electrolyte Content Faeces", Proceedings of the Royal Society of Medicine, 1965, pp. 1007-1009, vol. 58, No. 12.

Wrong, O. M., "Role of the Human Colon in Homeostasis," Scientific Basis of Medicine Annual Reviews, 1971, pp. 192-215.

Wrong, O., et al., "In Vivo Dialysis of Feces as a Method of Stool Analysis," Clinical Science, 1965, pp. 357-375, vol. 28.

Arakawa, T., et al., "Stabilization of Protein Structure by Sugars," Biochemistry, Dec. 7, 1982, pp. 6536-6544, vol. 21, No. 25.

Barrett, A. G. M., et al., "Trifluoromethyl Coordination and C—F Bond Activation at Calcium," Angewandte Chemie International Edition, 2007, pp. 6339-6342, vol. 46, No. 33.

Carpenter, J. F., et al., "Rational Design of Stable Lyophilized Protein Formulations: Some Practical Advice," Pharmaceutical Research, Aug. 1997, pp. 969-975 vol. 14, No. 8.

Chang, L., et al., "Mechanism of Protein Stabilization by Sugars During Freeze-Drying and Storage: Native Structure Preservation, Specific Interaction, and/or Immobilization in a Glassy Matrix?" Journal of Pharmaceutical Sciences, Jul. 2005, pp. 1427-1444, vol. 94, No. 7.

Cicerone, M. T., et al., "Substantially Improved Stability of Biological Agents in Dried Form, The Role of Glassy Dynamics in Preservation of Biopharmaceuticals," BioProcess International, Jan. 2003, pp. 36-47, vol. 1, No. 1.

Kim, C.-J., "Effects of Drug Solubility, Drug Loading, and Polymer Molecular Weight on Drug Release from Polyox(R) Tablets," Drug Development and Industrial Pharmacy, Jul. 1998, pp. 645-651, vol. 24, No. 7.

Makinen, K. K., et al., "Solubility of Calcium Salts, Enamel, and Hydroxyapatite in Aqueous Solutions of Simple Carbohydrates," Calcified Tissue International, Jan. 1984, pp. 64-71, vol. 36, No. 1.

Piedmonte, D. M., et al., "Sorbitol Crystallization Can Lead to Protein Aggregation in Frozen Protein Formulations," Pharmaceutical Research, Jan. 2007, pp. 136-146, vol. 24, No. 1.

Steenwijk, J., et al., "Long-Term Heat Stabilisation by (Natural) Polyols in Heavy Metal- and Zinc-Free Poly(Vinyl Chloride)," Polymer Degradation and Stability, 2006, pp. 52-59, vol. 91.

Van Es, D. S., et al., "The Compatibility of (Natural) Polyols with Heavy Metal- and Zinc-Free Poly(Vinyl Chloride): Their Effect on Rheology and Implications for Plate-Out," Polymer Degradation and Stability, 2008, pp. 50-58, vol. 93.

Yang, L., et al., "Physicochemical Aspects of Drug Delivery and Release From Polymer-Based Colloids," Current Opinion in Colloid & Interface Science, 2000, pp. 132-143, vol. 5.

Zabozlaev, A. A., et al., "Drug Synthesis Methods and Manufacturing Technology, Solubilization of Poorly Soluble Calcium Salts of Organic Acids with Sorbitol," Pharmaceutical Chemistry Journal, 2007, pp. 430-433, vol. 41, No. 8.

Office Action dated Jan. 24, 2012, issued for U.S. Appl. No. 12/545,812, 8 pages.

* cited by examiner

LINEAR POLYOL STABILIZED POLYFLUOROACRYLATE COMPOSITIONS

CROSS-REFERENCE TO RELATED APPLICATIONS

This application is a Non-Provisional Patent Application of U.S. Provisional Patent Application Ser. No. 61/165,899, filed Apr. 1, 2009, and U.S. Provisional Patent Application Ser. No. 61/091,097, filed Aug. 22, 2008, the entirety of which are herein incorporated by reference.

FIELD OF THE INVENTION

The present invention is directed to compositions of a stabilizing linear polyol and a salt of a crosslinked cation exchange polymer comprising a fluoro group and an acid group. These compositions are useful to bind potassium in the gastrointestinal tract.

BACKGROUND OF THE INVENTION

Potassium ($K^+$) is one of the most abundant intracellular cations. Potassium homeostasis is maintained predominantly through the regulation of renal excretion. Various medical conditions, such as decreased renal function, genitourinary disease, cancer, severe diabetes mellitus, congestive heart failure and/or the treatment of these conditions can lead to or predispose patients to hyperkalemia. Hyperkalemia can be treated with various cation exchange polymers including polyfluoroacrylic acid (polyFAA) as disclosed in WO 2005/097081.

Various polystyrene sulfonate cation exchange polymers (e.g., Kayexalate®, Argamate®, Kionex®) have been used to treat hyperkalemia in patients. These polymers and polymer compositions are known to have patient compliance issues, including dosing size and frequency, taste and/or texture, and gastric irritation. For example, in some patients, constipation develops, and sorbitol is thus commonly co-administered to avoid constipation, but this leads to diarrhea and other gastrointestinal side effects. It is also known that a wide variety of sugars can be used in pharmaceutical compositions. See, for example, EP 1785141.

Methods of reducing potassium and/or treatment of hyperkalemia have been found to raise patient compliance problems, in particular in chronic settings, which are solved by the present invention. Such problems include lack of tolerance of the therapeutically effective dose of polymeric binder (e.g., anorexia, nausea, gastric pain, vomiting and fecal impaction), dosing form (e.g., taste, mouth feel, etc.) and dose frequency (e.g., three times per day). The present invention solves these problems by providing a polymeric binder or a composition containing a polymeric binder that can be given once a day or twice a day without significant gastrointestinal side effects while retaining substantially similar efficacy. The methods of the present invention reduce the frequency and form of administration of potassium binder and increase tolerance, which will improve patient compliance, and potassium binding effectiveness.

It has been found that linear polyols in particular have a stabilizing effect during storage on crosslinked poly alpha-fluoroacrylic acid in its salt form.

SUMMARY OF THE INVENTION

The present invention provides a pharmaceutical composition that comprises a salt of a crosslinked cation exchange polymer and a linear polyol stabilizer. Optionally, moisture is added to the composition. The salt of a preferred crosslinked cation exchange polymer is the product of the polymerization of at least two, and optionally three, different monomer units and is stabilized with respect to fluoride release. Among the various aspects of the invention is a composition comprising a linear polyol and a salt of a crosslinked cation exchange polymer comprising a fluoro group and an acid group that is the product of the polymerization of at least two, and optionally three, different monomer units. Typically, one monomer comprises a fluoro group and an acid group and the other monomer is a difunctional arylene monomer or a difunctional alkylene, ether- or amide-containing monomer, or a combination thereof.

A further aspect of the invention is a pharmaceutical composition comprising a crosslinked cation exchange polymer salt and from about 10 wt. % to about 40 wt. % of a linear polyol based on the total weight of the composition. The crosslinked cation exchange polymer comprises structural units corresponding to Formulae 1 and 2, Formulae 1 and 3, or Formulae 1, 2, and 3, wherein Formula 1, Formula 2, and Formula 3 are represented by the following structures:

Formula 1

Formula 2

Formula 3 wherein $R_1$ and $R_2$ are each independently hydrogen, alkyl, cycloalkyl, or aryl; $A_1$ is carboxylic, phosphonic, or phosphoric; $X_1$ is arylene; and $X_2$ is alkylene, an ether moiety, or an amide moiety. In some instances, Formula 1, Formula 2, and Formula 3 are represented by the following structures:

Formula 1A

Formula 2A

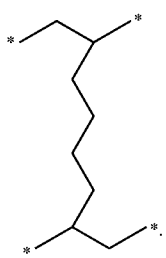

Formula 3A

Another aspect of the invention is a pharmaceutical composition comprising a crosslinked cation exchange polymer salt and an effective amount of a linear polyol sufficient to stabilize the polymer salt, wherein the salt of the crosslinked cation exchange polymer comprises structural units corresponding to Formulae 1 and 2, Formulae 1 and 3, or Formulae 1, 2, and 3. In some instances, the structural units of Formula 1, Formula 2 and Formula 3 correspond to Formula 1A, Formula 2A, and Formula 3A, respectively. Optionally, the composition further comprises moisture.

A further aspect is a pharmaceutical composition comprising a crosslinked cation exchange polymer salt and from about 10 wt. % to about 40 wt. % of a linear polyol based on the total weight of the composition, the crosslinked cation exchange polymer being a reaction product of a polymerization mixture comprising monomers of either (i) Formulae 11 and 22, (ii) Formulae 11 and 33, or (iii) Formulae 11, 22, and 33. Formula 11, Formula 22, and Formula 33 are represented by the following structures:

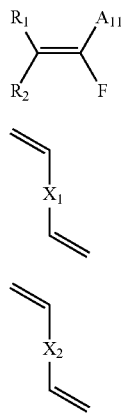

Formula 11

Formula 22

Formula 33 wherein $R_1$ and $R_2$ are each independently hydrogen, alkyl, cycloalkyl, or aryl; $A_{11}$ is an optionally protected carboxylic, phosphonic, or phosphoric; $X_1$ is arylene; and $X_2$ is alkylene, an ether moiety, or an amide moiety. In some instances, Formula 11, Formula 22, and Formula 33 are represented by the following structures:

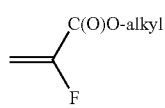

Formula 11A

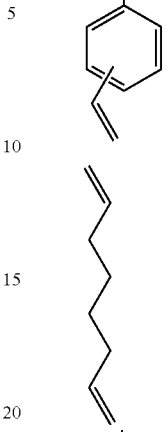

Formula 22A

Formula 33A

Another aspect of the invention is a pharmaceutical composition comprising a crosslinked cation exchange polymer salt and an effective amount of a linear polyol sufficient to stabilize the polymer salt, wherein the salt of the crosslinked cation exchange polymer is a reaction product of a polymerization mixture comprising monomers corresponding to Formulae 11 and 22, Formulae 11 and 33, or Formulae 11, 22, and 33. In some instances, Formula 1, Formula 2 and Formula 3 correspond to Formula 11A, Formula 22A, and Formula 33A, respectively. Optionally the composition further comprises moisture.

Yet another aspect is a method for removing potassium from the gastrointestinal tract of an animal subject in need thereof. The method comprises administering any one of the crosslinked cation exchange polymers or pharmaceutical compositions described herein to the subject, whereby the polymer or pharmaceutical composition passes through the gastrointestinal tract of the subject, and removes a therapeutically effective amount of potassium ion from the gastrointestinal tract of the subject. In some embodiments, the subject is a mammal, and preferably, a human.

A further aspect is a method for removing potassium from the gastrointestinal tract of an animal subject in need thereof, comprising administering an effective amount once per day or twice per day to the subject of a crosslinked cation exchange polymer or any pharmaceutical composition described herein, wherein the polymer comprises structural units corresponding to Formulae 1 and 2, Formulae 1 and 3, or Formulae 1, 2, and 3, wherein Formula 1, Formula 2, and Formula 3 are represented by the following structures:

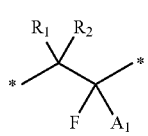

Formula 1

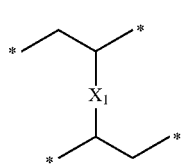

Formula 2

-continued

Formula 3

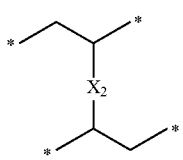

wherein $R_1$ and $R_2$ are each independently hydrogen, alkyl, cycloalkyl, or aryl; $A_1$ is carboxylic, phosphonic, or phosphoric; $X_1$ is arylene; and $X_2$ is alkylene, an ether moiety, or an amide moiety, wherein a daily amount of the polymer or composition has a potassium binding capacity of at least 75% of the binding capacity of the same polymer or composition administered at the same daily amount three times per day.

The present invention also provides a method of removing potassium in an animal subject in need thereof, comprising administering an effective amount once per day or twice per day to the subject of a crosslinked cation exchange polymer or any pharmaceutical composition described herein, wherein the polymer is the reaction product of a polymerization mixture comprising monomers of either (i) Formulae 11 and 22, (ii) Formulae 11 and 33, or (iii) Formulae 11, 22, and 33. Formula 11, Formula 22, and Formula 33 are represented by the following structures:

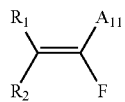

Formula 11

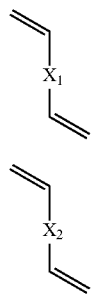

Formula 22

Formula 33 wherein $R_1$ and $R_2$ are each independently hydrogen, alkyl, cycloalkyl, or aryl; $A_{11}$ is an optionally protected carboxylic, phosphonic, or phosphoric; $X_1$ is arylene; and $X_2$ is alkylene, an ether moiety, or an amide moiety, wherein a daily amount of the polymer or the composition has a potassium binding capacity of at least 75% of the binding capacity of the same polymer or composition administered at the same daily amount three times per day.

In other embodiments, the present invention provides a method of removing potassium from the gastrointestinal tract of an animal subject in need thereof, comprising administering an effective amount once per day or twice per day to the subject of a daily amount of a crosslinked cation exchange polymer or a pharmaceutical composition as described herein, wherein either (1) less than 25% of subjects taking the polymer or composition once per day or twice per day experience mild or moderate gastrointestinal adverse events or (2) a daily amount of the polymer or composition has a potassium binding capacity of at least 75% of the same daily amount of the same polymer administered three times per day or (3) both.

It has also been found that use of a composition comprising a crosslinked aliphatic carboxylic polymer and an effective amount of, or in some instances from about 10 wt. % to about 40 wt. % of, a linear polyol has increased efficacy for removal of potassium as compared to a composition not containing the linear polyol. In this regard, increased efficacy is measured by the amount of fecal excretion of potassium. The compositions and/or methods of this invention include a composition comprising an effective amount, or in some instances from about 10 wt. % to about 40 wt. %, of a linear polyol, and a crosslinked aliphatic carboxylic polymer that extracts from an animal subject in need thereof about 5% more potassium as compared to the same dose and same administration frequency of the same polymer without stabilization by a linear polyol.

DETAILED DESCRIPTION

The present invention is directed to pharmaceutical compositions comprising a polyol and a salt of a crosslinked cation exchange polymer, with the polyol present in an amount sufficient to reduce the release of fluoride ion from the cation exchange polymer during storage. In some embodiments, the pharmaceutical compositions of this invention additionally comprise water also present in an amount sufficient to reduce or assist in the reduction of the release of fluoride ion from the cation exchange polymer during storage. Generally, the salt of a crosslinked cation exchange polymer comprised a fluoro group and an acid group is the product of the polymerization of at least two, and optionally three, different monomer units. Typically, one monomer comprises a fluoro group and an acid group and the other monomer is a difunctional arylene monomer or a difunctional alkylene, ether- or amide-containing monomer, or a combination thereof. These pharmaceutical compositions are useful to bind potassium in the gastrointestinal tract. In preferred embodiments, the linear polyol is a linear sugar alcohol. Increased efficacy, and/or tolerability in different dosing regimens, is seen as compared to compositions without the linear polyol, and optionally including water.

A linear polyol is added to the composition containing the salt of a crosslinked cation exchange polymer in an amount effective to stabilize the polymer salt, and generally from about 10 wt. % to about 40 wt. % linear polyol based on the total weight of the composition. The linear polyol is preferably a linear sugar (i.e, a linear sugar alcohol). The linear sugar alcohol is preferably selected from the group consisting of D-(+)arabitol, erythritol, glycerol, maltitol, D-mannitol, ribitol, D-sorbitol, xylitol, threitol, galactitol, isomalt, iditol, lactitol and combinations thereof, more preferably selected from the group consisting of D-(+)arabitol, erythritol, glycerol, maltitol, D-mannitol, ribitol, D-sorbitol, xylitol, and combinations thereof, and most preferably selected from the group consisting of xylitol, sorbitol, and a combination thereof. Preferably, the pharmaceutical composition contains from about 15 wt. % to about 35 wt. % stabilizing polyol based on the total weight of the composition. In various embodiments, this linear polyol concentration is sufficient to reduce the release of fluoride ion from the cation exchange polymer upon storage as compared to an otherwise identical composition containing no stabilizing polyol at the same temperature and storage time.

The moisture content of the composition can be balanced with the stabilizing linear polyol to provide a stabilized polymer within the composition. In general, as the moisture content of the composition increases, the concentration of polyol can be decreased. However, the moisture content should not rise so high as to prevent the composition from being free flowing during manufacturing or packaging operations. In general, the moisture content can range from about 1 to about 30 weight percent based on the total weight of the composition. More specifically, the moisture content can be from about 10 to about 25 wt. % based on the total weight of the composition of polymer, linear polyol and water. In one specific case, the pharmaceutical composition comprises about 10-40 wt. % linear polyol, about 1-30 wt. % water and the remainder crosslinked cation exchange polymer, with the weight percents based on the total weight of linear polyol, water and polymer. Also, in a specific case, the pharmaceutical composition comprises about 15 wt. % to about 35 wt. % linear polyol, about 10 wt. % to about 25 wt % water and the remainder crosslinked cation exchange polymer, with the weight percents based on the total weight of linear polyol, water and polymer. In another specific case, the pharmaceutical composition comprises from about 10 wt. % to about 40 wt. % linear polyol and the remainder crosslinked cation exchange polymer, with the weight percents based on the total weight of linear polyol and polymer.

The moisture content can be measured in a manner known to those of skill in the art. Moisture content in the composition may be determined by two methods: (a) thermogravimetric method via a moisture analyzer during in-process manufacturing or (b) measuring loss on drying in accordance with US Pharmacopeia (USP) <731>. The operating condition for the thermogravimetric method via moisture analyzer is 0.3 g of polymer composition heated at about 160° C. for about 45 min. The operating condition for the USP <731> method is 1.5-2 g of polymer composition heated to about 130° C. for about 16 hours under 25-35 mbar vacuum.

From a stabilizing viewpoint, the concentration of inorganic fluoride (e.g., from fluoride ion) in the pharmaceutical composition is less than about 1000 ppm, less than about 500 ppm or less than about 300 ppm under typical storage conditions. More particularly, the concentration of inorganic fluoride in the pharmaceutical composition is less than about 1000 ppm after storage at accelerated storage conditions (about 40° C. for about 6 weeks), less than about 500 ppm after room temperature storage (about 25° C. for about 6 weeks), or less than about 300 ppm after refrigerated storage (about 5° C. for about 6 weeks). Additionally, the concentration of inorganic fluoride in the pharmaceutical composition is generally 50% less and preferably 75% less than the concentration of inorganic fluoride in the otherwise identical composition containing no stabilizing polyol at the same temperature and storage time.

The pharmaceutical composition comprises a crosslinked carboxylic cation exchange polymer. Specifically, the composition includes a crosslinked cation exchange polymer comprising structural units corresponding to Formulae 1 and 2, Formulae 1 and 3, or Formulae 1, 2, and 3, wherein Formula 1, Formula 2, and Formula 3 are represented by the following structures:

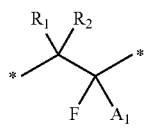

Formula 1

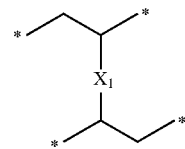

Formula 2

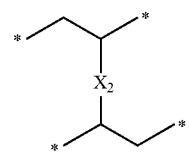

Formula 3 wherein $R_1$ and $R_2$ are each independently hydrogen, alkyl, cycloalkyl, or aryl; $A_1$ is carboxylic, phosphonic, or phosphoric; $X_1$ is arylene; and $X_2$ is alkylene, an ether moiety, or an amide moiety. More specifically, $R_1$ and $R_2$ are each independently hydrogen, alkyl, cycloalkyl, or aryl; $A_1$ is carboxylic, phosphonic, or phosphoric; $X_1$ is arylene; and $X_2$ is alkylene, an ether moiety, or an amide moiety.

When $X_2$ is an ether moiety, the ether moiety can be $-(CH_2)_d-O-(CH_2)_e-$ or $-(CH_2)_d-O-(CH_2)_e-(CH_2)_d-$, wherein d and e are independently an integer of 1 through 5. In some instances, d is an integer from 1 to 2 and e is an integer from 1 to 3. When $X_2$ is an amide moiety, the amide moiety can be $-C(O)-NH-(CH_2)_p-NH-C(O)-$ wherein p is an integer of 1 through 8. In some instances, p is an integer of 4 to 6.

The unit corresponding to Formula 2 can be derived from a difunctional crosslinking monomer having the formula $CH_2=CH-X_1-CH=CH_2$ wherein $X_1$ is as defined in connection with Formula 2. Further, the unit corresponding to Formula 3 can be derived from a difunctional crosslinking monomer having the formula $CH_2=CH-X_2-CH=CH_2$ wherein $X_2$ is as defined in connection with Formula 3.

In connection with Formula 1, in one embodiment, $R_1$ and $R_2$ are hydrogen and $A_1$ is carboxylic. In connection with Formula 2, in one embodiment, $X_1$ is an optionally substituted phenylene, and preferably phenylene. In connection with Formula 3, in one embodiment, $X_2$ is optionally substituted ethylene, propylene, butylene, pentylene, or hexylene; more specifically, $X_2$ is ethylene, propylene, butylene, pentylene, or hexylene; and preferably $X_2$ is butylene. In one specific embodiment, $R_1$ and $R_2$ are hydrogen, $A_1$ is carboxylic, $X_1$ is phenylene and $X_2$ is butylene.

In one embodiment, the crosslinked cation exchange polymer comprises at least about 80 wt. %, particularly at least about 85 wt. %, and more particularly at least about 90 wt. % or from about 80 wt. % to about 95 wt. %, from about 85 wt. % to about 95 wt. %, from about 85 wt. % to about 93 wt. % or from about 88 wt. % to about 92 wt. % of structural units corresponding to Formula 1 based on the total weight of the structural units as used in the polymerization mixture corresponding to (i) Formulae 1 and 2, (ii) Formulae 1 and 3, or (iii) Formulae 1, 2, and 3. Additionally, the polymer can comprise a unit of Formula 1 having a mole fraction of at least about 0.87 or from about 0.87 to about 0.94 or from about 0.90 to about 0.92 based on the total number of moles of the units corresponding to (i) Formulae 1 and 2, (ii) Formulae 1 and 3, or (iii) Formulae 1, 2, and 3.

In one embodiment, the polymer contains structural units of Formulae 1, 2, and 3 and has a weight ratio of the structural unit corresponding to Formula 2 to the structural unit corresponding to Formula 3 of from about 4:1 to about 1:4, from about 2:1 to 1:2, or about 1:1. Additionally, this polymer can have a mole ratio of the structural unit of Formula 2 to the structural unit of Formula 3 of from about 0.2:1 to about 7:1, from about 0.2:1 to about 3.5:1; from about 0.5:1 to about 1.3:1, from about 0.8 to about 0.9, or about 0.85:1.

Generally, the Formulae 1, 2 and 3 structural units of the terpolymer have specific ratios, for example, wherein the structural units corresponding to Formula 1 constitute at least about 85 wt. % or from about 80 to about 95 wt. %, from about 85 wt. % to about 93 wt. %, or from about 88 wt. % to about 92 wt. % based on the total weight of structural units of Formulae 1, 2, and 3 in the polymer, calculated based on the amounts of monomers of Formulae 11, 22, and 33 used in the polymerization reaction, and the weight ratio of the structural unit corresponding to Formula 2 to the structural unit corresponding to Formula 3 is from about 4:1 to about 1:4, or about 1:1. Further, the ratio of structural units when expressed as the mole fraction of the structural unit of Formula 1 in the polymer is at least about 0.87 or from about 0.87 to about 0.94, or from about 0.9 to about 0.92, based on the total number of moles of the structural units of Formulae 1, 2, and 3, and the mole ratio of the structural unit of Formula 2 to the structural unit of Formula 3 is from about 0.2:1 to about 7:1, from about 0.2:1 to about 3.5:1, or from about 0.8 to about 0.9; or 0.85:1; again these calculations are performed using the amounts of monomers of Formulae 11, 22, and 33 used in the polymerization reaction. It is not necessary to calculate conversion.

In some aspects, the crosslinked cation exchange polymer comprises units corresponding to (i) Formulae 1A and 2A, (ii) Formulae 1A and 3A, or (iii) Formulae 1A, 2A, and 3A, wherein Formulae 1A, 2A and 3A are generally represented by the following structures.

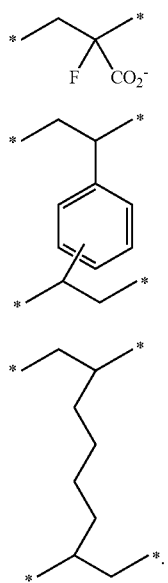

Formula 1A

Formula 2A

Formula 3A

In Formula 1 or 1A, the carboxylic acid is preferably in the salt form (i.e., balanced with a counter-ion such as $Ca^{2+}$, $Mg^{2+}$, $Na^+$, $NH_4^+$, and the like). Preferably, the carboxylic acid is in the salt form and balanced with a $Ca^{2+}$ counterion. When the carboxylic acid of the crosslinked cation exchange form is balanced with a divalent counterion, two carboxylic acid groups can be associated with the one divalent cation.

The structural units of the terpolymer can have specific ratios, for example, wherein the structural units corresponding to Formula 1A constitute at least about 85 wt. % or from about 80 to about 95 wt. %, from about 85 wt. % to about 93 wt. %, or from about 88 wt. % to about 92 wt. % based on the total weight of structural units of Formulae 1A, 2A, and 3A, calculated based on the amounts of monomers of Formulae 11A, 22A, and 33A used in the polymerization reaction, and the weight ratio of the structural unit corresponding to Formula 2A to the structural unit corresponding to Formula 3A is from about 4:1 to about 1:4, or about 1:1. Further, the ratio of structural units when expressed as the mole fraction of the structural unit of Formula 1A in the polymer is at least about 0.87 or from about 0.87 to about 0.94, or from about 0.9 to about 0.92 based on the total number of moles of the structural units of Formulae 1A, 2A, and 3A calculated from the amount of monomers of Formulae 11A, 22A, and 33A used in the polymerization reaction, and the mole ratio of the structural unit of Formula 2A to the structural unit of Formula 3A is from about 0.2:1 to about 7:1, from about 0.2:1 to about 3.5:1, from about 0.5:1 to about 1.3:1, from about 0.8:1 to about 0.9:1, or about 0.85:1.

The polymers described herein are generally random polymers wherein the exact order of the structural units of Formulae 1, 2, or 3 (derived from monomers of Formulae 11, 22, or 33), or 1A, 2A, or 3A (derived from monomers of Formulae 11A, 22A, or 33A) is not predetermined.

A cation exchange polymer derived from monomers of Formulae 11, 22, and 33, followed by hydrolysis, can have a structure represented as follows:

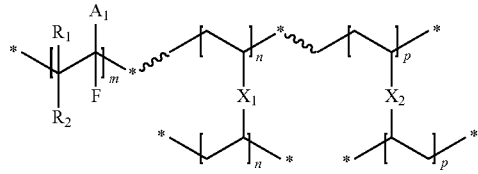

Formula 40 wherein $R_1$, $R_2$, $A_1$, $X_1$, and $X_2$ are as defined in connection with Formulae 1, 2, and 3 and m is in the range of from about 85 to about 93 mol %, n is in the range of from about 1 to about 10 mol % and p is in the range of from about 1 to about 10 mol %, calculated based on the ratios of monomers added to the polymerization mixture. The wavy bonds in the polymer structures of Formula 40 are included to represent the random attachment of structural units to one another wherein the structural unit of Formula 1 can be attached to another structural unit of Formula 1, a structural unit of Formula 2, or a structural unit of Formula 3; the structural units of Formulae 2 and 3 have the same range of attachment possibilities.

Using the polymerization process described herein, with monomers generally represented by Formulae 11A, 22A and 33A, followed by hydrolysis and calcium ion exchange, a polymer represented by the general structure shown below is obtained:

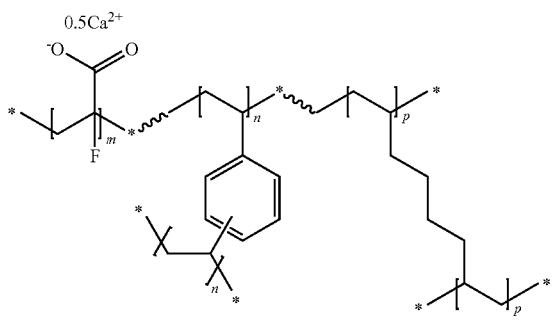

Formula 40A wherein m is in the range of from about 85 to about 93 mol %, n is in the range of from about 1 to about 10 mol % and p is in the range of from about 1 to about 10 mol %, calculated based on the ratios of monomers added to the polymerization mixture. The wavy bonds in the polymer structures of Formula 40A are included to represent the random attachment of structural units to one another wherein the structural unit of Formula 1A can be attached to another structural unit of Formula 1A, a structural unit of Formula 2A, or a structural unit of Formula 3A; the structural units of Formulae 2A and 3A have the same range of attachment possibilities.

The crosslinked cation exchange polymer is generally the reaction product of a polymerization mixture that is subjected to polymerization conditions. The polymerization mixture may also contain components that are not chemically incorporated into the polymer. The crosslinked cation exchange polymer typically comprises a fluoro group and an acid group that is the product of the polymerization of at least two, and optionally three, different monomer units where one monomer comprises a fluoro group and an acid group and the other monomer is a difunctional arylene monomer or a difunctional alkylene, ether- or amide-containing monomer, or a combination thereof. More specifically, the crosslinked cation exchange polymer can be a reaction product of a polymerization mixture comprising monomers of (i) Formulae 11 and 22, (ii) Formulae 11 and 33, or (iii) Formulae 11, 22, and 33. The monomers of Formulae 11, 22, and 33 are generally represented by

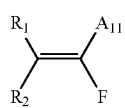

Formula 11

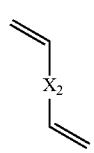

Formula 22

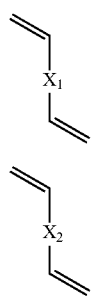

Formula 33 wherein $R_1$ and $R_2$ are as defined in connection with Formula 1, $X_1$ is as defined in connection with Formula 2, $X_2$ is as defined in connection with Formula 3, and $A_{11}$ is an optionally protected carboxylic, phosphonic, or phosphoric. In a preferred embodiment, $A_{11}$ is a protected carboxylic, phosphonic, or phosphoric. The product of a polymerization reaction comprising monomers of (i) Formulae 11 and 22, (ii) Formulae 11 and 33, or (iii) Formulae 11, 22, and 33 comprises a polymer having optionally protected acid groups and comprising units corresponding to Formula 10 and units corresponding to Formulae 2 and 3. Polymer products having protected acid groups can be hydrolyzed to form a polymer having unprotected acid groups and comprising units corresponding to Formulae 1, 2, and 3. The structural units generally represented by Formula 10 have the structure

Formula 10 wherein $R_1$, $R_2$, and $A_{11}$ are as defined in connection with Formula 11.

In preferred embodiments of any of the methods of the invention wherein the crosslinked cation exchange polymer is a reaction product of a polymerization mixture of monomers, A11 is a protected carboxylic, phosphonic, or phosphoric. The polymer formed in the polymerization reaction contains protected carboxylic, phosphonic, or phosphoric groups. A hydrolysis agent can be added to the polymer formed in the polymerization reaction to hydrolyze these protected groups, converting them to carboxylic, phosphonic, or phosphoric groups, or other methods of deprotection well known in the art can be used. The hydrolyzed polymer is preferably subjected to ion exchange to obtain a preferred polymer salt for therapeutic use.

In one embodiment, the reaction mixture comprises at least about 80 wt. %, particularly at least about 85 wt. %, and more particularly at least about 90 wt. % or from about 80 wt. % to about 95 wt. %, from about 85 wt. % to about 95 wt. %, from about 85 wt. % to about 93 wt. % or from about 88 wt. % to about 92 wt. % of monomers corresponding to Formula 11 based on the total weight of the monomers corresponding to (i) Formulae 11 and 22, (ii) Formulae 11 and 33, or (iii) Formulae 11, 22, and 33. Additionally, the reaction mixture can comprise a unit of Formula 11 having a mole fraction of at least about 0.87 or from about 0.87 to about 0.94 based on the total number of moles of the monomers corresponding to (i) Formulae 11 and 22, (ii) Formulae 11 and 33, or (iii) Formulae 11, 22, and 33.

In one embodiment, the polymerization reaction mixture contains monomers of Formulae 11, 22, and 33 and has a weight ratio of the monomer corresponding to Formula 22 to the monomer corresponding to Formula 33 from about 4:1 to about 1:4, from about 2:1 to 1:2, or about 1:1. Additionally, this mixture can have a mole ratio of the monomer of Formula 22 to the monomer of Formula 33 from about 0.2:1 to about 7:1, from 0.2:1 to 3.5:1, from about 0.5:1 to about 1.3:1, from about 0.8:1 to about 0.9:1, or about 0.85:1.

Particular crosslinked cation exchange polymers are the reaction product of a polymerization mixture comprising monomers of (i) Formulae 11 and 22, (ii) Formulae 11 and 33, or (iii) Formulae 11, 22, and 33. The monomers are generally represented by Formulae 11A, 22A, and 33A having the structure:

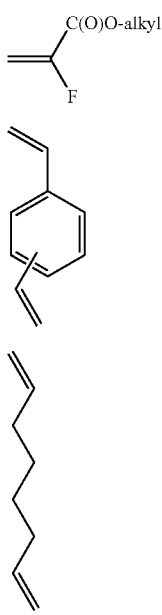

Formula 11A

Formula 22A

Formula 33A wherein alkyl is preferably selected from methyl, ethyl, propyl, iso-propyl, butyl, iso-butyl, sec-butyl, tert-butyl, pentyl, iso-pentyl, sec-pentyl, or tert-pentyl. Most preferably, the alkyl group is methyl or tert-butyl. The —O-alkyl moiety protects the carboxyl moiety from reacting with other reactive moieties during the polymerization reaction and can be removed by hydrolysis or other deprotection methods as described in more detail below.

Further, the polymerization reaction mixture contains at least about 80 wt. %, particularly at least about 85 wt. %, and more particularly at least about 90 wt. % or from about 80 wt. % to about 95 wt. %, from about 85 wt. % to about 95 wt. %, from about 85 wt. % to about 93 wt. % or from about 88 wt. % to about 92 wt. % of monomers corresponding to Formula 11A based on the total weight of the monomers which are generally represented by (i) Formulae 11A and 22A, (ii) Formulae 11A and 33A, or (iii) Formulae 11A, 22A, and 33A. Additionally, the reaction mixture can comprise a unit of Formula 11A having a mole fraction of at least about 0.87 or from about 0.87 to about 0.94 or from about 0.9 to about 0.92 based on the total number of moles of the monomers present in the polymer which are generally represented by (i) Formulae 11A and 22A, (ii) Formulae 11A and 33A, or (iii) Formulae 11A, 22A, and 33A.

In some instances, the reaction mixture contains monomers of Formulae 11, 22, and 33 and the weight ratio of the monomer generally represented by Formula 22A to the monomer generally represented by Formula 33A of from about 4:1 to about 1:4 or about 1:1. Also, this mixture has a mole ratio of the monomer of Formula 22A to the monomer of Formula 33A of from about 0.2:1 to about 7:1, from about 0.2:1 to about 3.5:1, from about 0.5:1 to about 1.3:1, from about 0.8:1 to about 0.9:1, or about 0.85:1.

In a preferred embodiment, an initiated polymerization reaction is employed where a polymerization initiator is used in the polymerization reaction mixture to aid initiation of the polymerization reaction. When preparing poly(methylfluoroacrylate) or (polyMeFA) or any other crosslinked cation exchange polymer used in the invention in a suspension polymerization reaction, the nature of the free radical initiator plays a role in the quality of the suspension in terms of polymer particle stability, yield of polymer particles, and the polymer particle shape. Use of water-insoluble free radical initiators, such as lauroyl peroxide, can produce polymer particles in a high yield. Without being bound by any particular theory, it is believed that a water-insoluble free radical initiator initiates polymerization primarily within the dispersed phase containing the monomers of Formulae 11 and 22, 11 and 33, or 11, 22, and 33. Such a reaction scheme provides polymer particles rather than a bulk polymer gel. Thus, the process uses free radical initiators with water solubility lower than 0.1 g/L, particularly lower than 0.01 g/L. In particular embodiments, polymethylfluoroacrylate particles are produced with a combination of a low water solubility free radical initiator and the presence of a salt in the aqueous phase, such as sodium chloride.

The polymerization initiator can be chosen from a variety of classes of initiators. For instance, initiators that generate polymer imitating radicals upon exposure to heat include peroxides, persulfates or azo type initiators (e.g., 2,2'-azobis (2-methylpropionitrile), lauroyl peroxide (LPO), tert-butyl hydro peroxide, dimethyl-2,2'-azobis(2-methylpropionate), 2,2'-azobis(2-methyl-N-(2-hydroxyethyl)propionamide), 2,2'-azobis(2-(2-imidazolin-2-yl)propane), (2,2''-azo bis(2, 4-dimethylvaleronitrile), azobisisobutyronitrile (AIBN) or a combination thereof. Another class of polymer initiating radicals is radicals generated from redox reactions, such as persulfates and amines Radicals can also be generated by exposing certain initiators to UV light or exposure to air.

For those polymerization reactions that contain additional components in the polymerization mixture that are not intended to be incorporated into the polymer, such additional components typically comprise surfactants, solvents, salts, buffers, aqueous phase polymerization inhibitors and/or other components known to those of skill in the art. When the polymerization is carried out in a suspension mode, the additional components may be contained in an aqueous phase while the monomers and initiator may be contained in an organic phase. When an aqueous phase is present, the aqueous phase may be comprised of water, surfactants, stabilizers, buffers, salts, and polymerization inhibitors. A surfactant may be selected from the group consisting of anionic, cationic, nonionic, amphoteric, zwitterionic, or a combination thereof. Anionic surfactants are typically based on sulfate, sulfonate or carboxylate anions. These surfactants include, sodium dodecyl sulfate (SDS), ammonium lauryl sulfate, other alkyl sulfate salts, sodium laureth sulfate (or sodium lauryl ether sulfate (SLES)), N-lauroylsarcosine sodium salt, lauryldimethylamine-oxide (LDAO), ethyltrimethylammoniumbromide (CTAB), bis(2-ethylhexyl)sulfosuccinate sodium salt, alkyl benzene sulfonate, soaps, fatty acid salts, or a combination thereof. Cationic surfactants, for example, contain quaternary ammonium cations. These surfactants are cetyl trimethylammonium bromide (CTAB or hexadecyl trimethyl ammonium bromide), cetylpyridinium chloride (CPC), polyethoxylated tallow amine (POEA), benzalkonium chloride (BAC), benzethonium chloride (BZT), or a combination thereof. Zwitterionic or amphoteric surfactants include dodecyl betaine, dodecyl dimethylamine oxide, cocamidopropyl betaine, coco ampho glycinate, or a combination thereof. Nonionic surfactants include alkyl poly(ethylene oxide), copolymers of poly(ethylene oxide) and poly(propylene oxide) (commercially called Poloxamers or Poloxamines), alkyl polyglucosides (including octyl glucoside, decyl maltoside, fatty alcohols, cetyl alcohol, oleyl alcohol, cocamide MEA, cocamide DEA), or a combination thereof. Other pharmaceutically acceptable surfactants are well known in the art and are described in McCutcheon's Emulsifiers and Detergents, N. American Edition (2007).

Polymerization reaction stabilizers may be selected from the group consisting of organic polymers and inorganic particulate stabilizers. Examples include polyvinyl alcohol-co-vinylacetate and its range of hydrolyzed products, polyvinylacetate, polyvinylpyrolidinone, salts of polyacrylic acid, cellulose ethers, natural gums, or a combination thereof.

Buffers may be selected from the group consisting of for example, 4-2-hydroxyethyl-1-piperazineethanesulfonic acid, 2-{[tris(hydroxymethyl)methyl]amino}ethanesulfonic acid, 3-(N-morpholino)propanesulfonic acid, piperazine-N,N'-bis(2-ethanesulfonic acid), sodium phosphate dibasic heptahydrate, sodium phosphate monobasic monohydrate or a combination thereof.

Polymerization reaction salts may be selected from the group consisting of potassium chloride, calcium chloride, potassium bromide, sodium bromide, sodium bicarbonate, ammonium peroxodisulfate, or a combination thereof.

Polymerization inhibitors may be used as known in the art and selected from the group consisting of 1,1,3-tris(2-methyl-4-hydroxy-5-tert-butylphenyl)butane, 1,3,5-trimethyl-2,4,6-tris(3,5-di-tert-butyl-4-hydroxybenzyl)benzene, 1-aza-3,7-dioxabicyclo[3.3.0]octane-5-methanol, 2,2'-ethylidene-bis(4,6-di-tert-butylphenol), 2,2'-ethylidenebis(4,6-di-tert-butylphenyl) fluorophosphite, 2,2'-methylenebis(6-tert-butyl-4-ethylphenol), 2,2'-methylenebis(6-tert-butyl-4-methylphenol), 2,5-di-tert-butyl-4-methoxyphenol, 2,6-di-tert-butyl-4-(dimethylaminomethyl)phenol, 2-heptanone oxime, 3,3',5,5'-tetramethylbiphenyl-4,4'-diol, 3,9-bis(2,4-dicumylphenoxy)-2,4,8,10-tetraoxa-3,9-diphosphaspiro[5.5]undecane, 4,4-dimethyloxazolidine, 4-methyl-2-pentanone oxime, 5-ethyl-1-aza-3,7-dioxabicyclo[3.3.0]octane, 6,6'-dihydroxy-5,5'-dimethoxy-[1,1'-biphenyl]-3,3'-dicarboxaldehyde, distearyl-3,3'-thiodipropionate, ditetradecyl-3,3'-thiodipropionate, ditridecyl-3,3'-thiodipropionate, octadecyl-3-(3,5-di-tert-butyl-4-hydroxyphenyl)propionate, pentaerythritol tetrakis(3,5-di-tert-butyl-4-hydroxyhydrocinnamate), poly(1,2-dihydro-2,2,4-trimethylquinoline), sodium D-isoascorbate monohydrate, tetrakis(2,4-di-tert-butylphenyl)-4,4'-biphenyldiphosphonite, tris(3,5-di-tert-butyl-4-hydroxybenzyl) isocyanurate, tris(4-tert-butyl-3-hydroxy-2,6-dimethylbenzyl) isocyanurate, sodium nitrite or a combination thereof.

Generally, the polymerization mixture is subjected to polymerization conditions. While suspension polymerization is preferred, as already discussed herein, the polymers used in this invention may also be prepared in bulk, solution or emulsion polymerization processes. The details of such processes are within the skill of one of ordinary skill in the art based on the disclosure of this invention. The polymerization conditions typically include polymerization reaction temperatures, pressures, mixing and reactor geometry, sequence and rate of addition of polymerization mixtures and the like. Polymerization temperatures are typically in the range of from about 50 to 100° C. Polymerization pressures are typically run at atmospheric pressure, but can be run at higher pressures (for example 130 PSI of nitrogen). Polymerization mixing depends on the scale of the polymerization and the equipment used, and is within the skill of one of ordinary skill in the art. Various alpha-fluoroacrylate polymers and the synthesis of these polymers are described in U.S. Patent Application Publication No. 2005/0220752, herein incorporated by reference.

As described in more detail in connection with the examples herein, in various particular embodiments, the crosslinked cation exchange polymer can be synthesized by preparing an organic phase and an aqueous phase. The organic phase typically contains a polymerization initiator and (i) a monomer of Formula 11 and a monomer of Formula 22, (ii) a monomer of Formula 11 and a monomer of Formula 33, or (iii) monomers of Formulae 11, 22, and 33. The aqueous phase generally contains a polymerization suspension stabilizer, a water soluble salt, water, and optionally a buffer. The organic phase and the aqueous phase are then combined and stirred under nitrogen. The mixture is generally heated to about 60° C. to about 80° C. for about 2.5 to about 3.5 hours, allowed to rise up to 95° C. after polymerization is initiated, and then cooled to room temperature. After cooling, the aqueous phase is removed. Water is added to the mixture, the mixture is stirred, and the resulting solid is filtered. The solid is washed with water, alcohol, or alcohol/water mixtures.

As described above, polymerization suspension stabilizers, such as polyvinyl alcohol, are used to prevent coalescence of particles during the polymerization process. Further, it has been observed that the addition of sodium chloride in the aqueous phase decreased coalescence and particle aggregation. Other suitable salts for this purpose include salts that are soluble in the aqueous phase. In this embodiment, water soluble salts are added at a concentration of from about 0.1 wt. % to about 10 wt. %, particularly from about 2 wt. % to about 5 wt. %, and even more particularly from about 3 wt. % to about 4 wt. %.

Preferably, an organic phase of methyl 2-fluoroacrylate (90 wt. %), 1,7-octadiene (5 wt. %) and divinylbenzene (5 wt. %) is prepared and 0.5 wt. % of lauroyl peroxide is added to initiate the polymerization reaction. Additionally, an aqueous phase of water, polyvinyl alcohol, phosphates, sodium chloride, and sodium nitrite is prepared. Under nitrogen and while keeping the temperature below about 30° C., the aqueous and organic phases are mixed together. Once mixed completely, the reaction mixture is gradually heated with continuous stirring. After the polymerization reaction is initiated, the temperature of the reaction mixture is allowed to rise up to about 95° C. Once the polymerization reaction is complete, the reaction mixture is cooled to room temperature and the aqueous phase is removed. The solid can be isolated by filtration once water is added to the mixture. The filtered solid is washed with water and then with a methanol/water mixture. The resulting product is a crosslinked (methyl 2-fluoroacrylate)-divinylbenzene-1,7-octadiene terpolymer.

As discussed herein, after polymerization, the product may be hydrolyzed or otherwise deprotected by methods known in the art. For hydrolysis of the polymer having ester groups to form a polymer having carboxylic acid groups, preferably, the polymer is hydrolyzed with a strong base (e.g., NaOH, KOH, $Mg(OH)_2$ or $Ca(OH)_2$) to remove the alkyl (e.g., methyl) group and form the carboxylate salt. Alternatively, the polymer can be hydrolyzed with a strong acid (e.g., HCl) to form the carboxylate salt. Preferably, the (methyl 2-fluoroacrylate)-divinylbenzene-1,7-octadiene terpolymer is hydrolyzed with an excess of aqueous sodium hydroxide solution at a temperature from about 30° C. to about 100° C. to yield (sodium 2-fluoroacrylate)-divinylbenzene-1,7-octadiene terpolymer. Typically, the hydrolysis reaction is carried out for about 15 to 25 hours. After hydrolysis, the solid is filtered and washed with water and/or an alcohol.

The cation of the polymer salt formed in the hydrolysis reaction or other deprotection step depends on the base used in that step. For example, when sodium hydroxide is used as the base, the sodium salt of the polymer is formed. This sodium ion can be exchanged for another cation by contacting the sodium salt with an excess of an aqueous metal salt to yield an insoluble solid of the desired polymer salt. After the desired ion exchange, the product is washed with an alcohol and/or water and dried directly or dried after a dewatering treatment with denatured alcohol; preferably, the product is washed with water and dried directly. For example, the sodium salt of the cation exchange polymer is converted to the calcium salt by washing with a solution that substitutes calcium for sodium, for example, by using calcium chloride, calcium acetate, calcium lactate gluconate, or a combination thereof. And, more specifically, to exchange sodium ions for calcium ions, the (sodium 2-fluoroacrylate)-divinylbenzene-1,7-octadiene terpolymer is contacted with an excess of aqueous calcium chloride to yield an insoluble solid of crosslinked (calcium 2-fluoroacrylate)-divinylbenzene-1,7-octadiene terpolymer.

Using this suspension polymerization process, crosslinked polyMeFA polymer is isolated in good yield, generally above about 85%, more specifically above about 90%, and even more specifically above about 93%. The yield of the second step (i.e., hydrolysis) preferably occurs in 100%, providing an overall yield above about 85%, more specifically above about 90%, and even more specifically above about 93%.

To add the linear polyol to the composition, the salt of the polymer is slurried with an aqueous solution of polyol (e.g., sorbitol), typically with the slurry containing an excess amount of polyol based on polymer weight. Performing this step can reduce inorganic fluoride in the composition. The slurry is maintained under conditions known to those of skill in the art, such as for at least 3 hours and ambient temperature and pressure. The solids are then filtered off and dried to desired moisture content.

The compositions of the invention are tested for their characteristics and properties using a variety of established testing procedures. For example, the percent inorganic fluoride in the composition is tested by mixing a dried sample of composition with C-Wax in a defined proportion, and making a pellet by pressing it with a force of about 40 kN in an aluminum cup. Percent fluorine content is analyzed by X-ray fluorescence in a manner known to those of skill in the art, for example, using a Bruker AXS SRS 3400 (Bruker AXS, Wisconsin). In general, the amount of organic fluorine in the composition is less than 25 wt. %, preferably less than 20 wt. %, more preferably 7 wt. % to 25 wt. % and most preferably 7 wt. % to 20 wt. % based on the total weight of the composition. The percent calcium in the composition is tested after extraction with an appropriate acid (e.g., 3M hydrochloric acid) using inductively coupled plasma optical emission spectroscopy (ICP-OES) analysis in a manner known to those of skill in the art, for example, using a Thermo IRIS Intrepid II XSP (Thermo Scientific, Waltham, Mass.). In general, the amount of calcium in the polymer is in the range of from about 8 wt. % to about 25 wt. %, and preferably about 10 wt. % to about 20 wt. %, based on the total weight of the polymer.

Also for example, the potassium binding capacity can be used for polymer or composition characterization. In this example, the potassium binding capacity is performed in vitro by weighing and transferring approximately 300 mg of a dried sample of polymer or composition into a 40 mL screw-top vial, and then adding a calculated volume of 200 mM KCl solution to achieve a concentration of 20 mg/mL of test substance. The vial is shaken vigorously for two hours, and the supernatant is filtered through a 0.45 μm filter followed by dilution to 1:20 in water. The supernatant is analyzed for potassium concentration via ICP-OES, and the potassium binding is calculated using the following formula.

$$\text{Potassium binding} = \frac{20(\text{dilution factor})}{20 \text{ mg/mL (sample } conc)} \times ([K]_{blank} - [K]_{sample}) \frac{\text{mmol } K}{\text{g polymer}}$$

One aspect of the invention is a method of removing potassium ions from the gastrointestinal tract of an animal subject in need thereof with a crosslinked cation exchange polymer or a pharmaceutical composition of the invention. The crosslinked cation exchange polymer generally has a high overall exchange capacity. The overall exchange capacity is the maximum amount of cations bound by the cation exchange polymer measured in mEq/g. A higher exchange capacity is desired as it is a measure of the density of acid groups in the polymer and the more acid groups per unit weight, the greater the overall exchange capacity of the polymer.

The crosslinked cation exchange polymers and the compositions comprising linear polyol and crosslinked cation exchange polymer also generally have a high binding capacity for potassium. In particular, the in vivo binding capacity is relevant to therapeutic benefit in a patient. Generally, a higher in vivo binding capacity results in a more pronounced therapeutic effect. However, since patients can have a wide range of responses to the administration of cation exchange polymers, one measure of the in vivo binding capacity for potassium is the average in vivo binding capacity calculated over a sample group. The term "high capacity" as used herein encompasses an average in vivo binding of about 1.0 mEq or more of potassium per gram of polymer.

One measure of the in vivo potassium binding capacity is the use of ex vivo human aspirates. For this method, healthy patients are given a meal as a digestion mimic and aliquots of chyme are then sampled using a tube placed in the lumen of the small intestine and other portions of the intestines. For example, normal subjects are intubated with a double lumen polyvinyl tube, with a mercury weighted bag attached to the end of the tube to facilitate movement of the tube into the small intestine. One aspiration aperture of the double lumen tube is located in the stomach and the other aperture is at the Ligament of Treitz (in the upper jejunum). Placement takes place with the use of fluoroscopy. After the tube is placed, 550 mL of a liquid standard test meal (supplemented with a marker, polyethylene glycol (PEG)-2 g/550 mL) is infused into the stomach through the gastric aperture at a rate of 22 mL per minute. It requires approximately 25 minutes for the entire meal to reach the stomach. This rate of ingestion simulates the duration of time required to eat normal meals. Jejunal chyme is aspirated from the tube whose lumen is located at the Ligament of Treitz. This fluid is collected continuously during 30-minute intervals for a two and a half hour period. This process results in five specimens that are mixed, measured for volume, and lyophilized.

The potassium binding procedure is identical to the one described below with the non-interfering buffer experiment, except that the ex vivo aspirate liquid is used (after reconstitution of the freeze-dried material in the proper amount of de-ionized water). The binding capacity in the ex vivo aspirate (VA) is calculated from the concentration of potassium in the aspirate with and without polymer. In some embodiments, the average ex vivo potassium binding capacity of a human gastrointestinal aspirate can be equal to or more than about 0.7 mEq per gram of polymer. More specifically, the ex vivo potassium binding capacity of a human gastrointestinal aspirate is about 0.8 mEq or more per gram, more particularly is about 1.0 mEq or more per gram, even more particularly is about 1.2 mEq or more per gram, and most particularly is about 1.5 mEq or more per gram.

Another measure of the in vivo binding capacity for potassium is the in vitro binding capacity for potassium in non-interfering environment or an interfering environment at a particular pH. In a non-interfering environment, the crosslinked cation exchange polymer is placed in a solution having potassium ions as the only cation. This solution is preferably at an appropriate GI physiological pH (e.g., about 6.5). The in vitro binding capacity for potassium in a non-interfering environment is a measure of the total binding capacity for cations.

Further, in an interfering environment, the environment contains cations in concentrations relevant to the typical concentrations in the gastrointestinal tract and is at physiological pH (e.g., about 6.5). In the interfering environment, it is preferred that the polymer or the pharmaceutical composition exhibit selective binding for potassium ions.

In some embodiments, the in vitro potassium binding capacity is determined in solutions with a pH of about 5.5 or more. In various embodiments, in vitro potassium binding capacity in a pH of about 5.5 or more is equal to or more than 6 mEq per gram of polymer. A particular range of in vitro potassium binding capacity in a pH of about 5.5 or more is about 6 mEq to about 12 mEq per gram of polymer. Preferably the in vitro potassium binding capacity in a pH of about 5.5 or more is equal to about 6 mEq or more per gram, more particularly is about 7 mEq or more per gram, and even more particularly is about 8 mEq or more per gram.

The higher capacity of the polymer may enable the administration of a lower dose of the pharmaceutical composition. Typically the dose of the polymer used to obtain the desired therapeutic and/or prophylactic benefits is about 0.5 gram/day to about 60 grams/day. A particular dose range is about 5 grams/day to about 60 grams/day, and more particularly is about 5 grams/day to about 30 grams/day. In various administration protocols, the dose is administered about three times a day, for example, with meals. In other protocols, the dose is administered once a day or twice a day. These doses can be for chronic or acute administration.

Polymers of the invention are crosslinked materials, meaning that they do not generally dissolve in solvents, and, at most, swell in solvents. As used herein, "swelling ratio" refers to the number of grams of solvent taken up by one gram of otherwise non-solvated crosslinked polymer when equilibrated in an aqueous environment. When more than one measurement of swelling is taken for a given polymer, the mean of the measurements is taken to be the swelling ratio.

The swelling ratio in physiological isotonic buffer, representative of the gastrointestinal tract, is typically in the range of about 1 to about 7, specifically about 1 to 5; more particularly about 1 to 2. In some embodiments, crosslinked cation exchange polymers of the invention have a swelling ratio of less than 5, or less than about 4, or less than about 3, or less than about 2.5, or less than about 2.

Generally, the polymers and pharmaceutical compositions described herein retain a significant amount of the bound potassium, and specifically, the potassium bound by the polymer is not released prior to excretion of the polymer in the feces. The term "significant amount" as used herein is not intended to mean that the entire amount of the bound potassium is retained prior to excretion. A sufficient amount of the bound potassium is retained, such that a therapeutic and/or prophylactic benefit is obtained. Particular amounts of bound potassium that can be retained range from about 5% to about 100%. The polymer or pharmaceutical composition should retain about 25% of the bound potassium, more particularly about 50%, even more particularly about 75% and most particularly retain about 100% of the bound potassium. The period of retention is generally during the time that the polymer or composition is being used therapeutically. In the embodiment in which the polymer or composition is used to bind and remove potassium from the gastrointestinal tract, the retention period is the time of residence of the polymer or composition in the gastrointestinal tract and more particularly the average residence time in the colon.

Generally, the cation exchange polymers are not significantly absorbed from the gastrointestinal tract. Depending upon the size distribution of the cation exchange polymer particles, clinically insignificant amounts of the polymers may be absorbed. More specifically, about 90% or more of the polymer is not absorbed, about 95% or more is not absorbed, even more specifically about 97% or more is not absorbed, and most specifically about 98% or more of the polymer is not absorbed.

In some embodiments of the invention, the polymers used in the invention will be administered unformulated (i.e., containing no additional carriers or other components). In other instances, a pharmaceutical composition containing the polymer, a stabilizing linear polyol and optionally water will be administered as described herein.

The methods, polymers and compositions described herein are suitable for removal of potassium from a patient wherein a patient is in need of such potassium removal. For example, patients experiencing hyperkalemia caused by disease and/or use of certain drugs benefit from such potassium removal. Further, patients at risk for developing high serum potassium concentrations through use of agents that cause potassium retention could be in need of potassium removal. The methods described herein are applicable to these patients regardless of the underlying condition that is causing the high serum potassium levels.

Dosing regimens for chronic treatment of hyperkalemia can increase compliance by patients, particularly for crosslinked cation exchange polymers or compositions of the invention that are taken in gram quantities. The present invention is also directed to methods of chronically removing potassium from an animal subject in need thereof, and in particular chronically treating hyperkalemia with a potassium binder that is a crosslinked aliphatic carboxylic polymer, and preferably a pharmaceutical composition comprising a crosslinked cation exchange polymer and a linear polyol as described herein.

It has now been found that when using the crosslinked cation exchange polymers and the compositions of the present invention, a once-a-day dose is substantially equivalent to a twice-a-day dose, which is also substantially equivalent to a three-times-a-day dose. Generally, the once per day or twice per day administration of a daily amount of the polymer or the composition, has a potassium binding capacity of at least 75% of the binding capacity of the same polymer or composition administered at the same daily amount three times per day. More specifically, the once per day or twice per day administration of a daily amount of the polymer or the composition has a potassium binding capacity of at least 80, 85, 90 or 95% of the binding capacity of the same polymer or composition administered at the same daily amount three times per day. Even more specifically, the once per day or twice per day administration of a daily amount of the polymer or the composition has a potassium binding capacity of at least 80% of the binding capacity of the same polymer or composition administered at the same daily amount three times per day. And even more specifically, the once per day or twice per day administration of a daily amount of the polymer or the composition has a potassium binding capacity of at least 90% of the binding capacity of the same polymer or composition administered at the same daily amount three times per day. Most preferably, the once per day or twice per day administration of a daily amount of the polymer or the composition has a potassium binding capacity that is not statistically significantly different from the binding capacity of the same polymer or composition at the same daily amount administered three times per day.

Additionally, the invention is directed to methods of removing potassium from an animal subject by administering a crosslinked cation exchange polymer or a pharmaceutical composition comprising a crosslinked cation exchange polymer and an effective amount or from about 10 wt. % to about 40 wt. % of a linear polyol to the subject once a day, wherein less than 25% of subjects taking the polymer or composition once per day experience mild or moderate gastrointestinal adverse events. Gastrointestinal adverse events may include flatulence, diarrhea, abdominal pain, constipation, stomatitis, nausea and/or vomiting. In some aspects, the polymer or composition is administered twice a day and less than 25% of subjects taking the polymer or composition twice per day experience mild or moderate gastrointestinal adverse events. In some instances, the subjects taking the polymer or composition once per day or twice per day experience no severe gastrointestinal adverse events. The crosslinked cation exchange polymers or pharmaceutical compositions of the present invention have about 50% or more tolerability as compared to the same polymer or composition of the same daily amount administered three times a day. For example, for every two patients in which administration of the polymer three times a day is well tolerated, there is at least one patient in which administration of the polymer once a day or twice a day is well tolerated. The crosslinked cation exchange polymers or pharmaceutical compositions have about 75% or more tolerability as compared to the same polymer or composition of the same daily amount administered three times a day. It is also a feature of this invention that the cation exchange polymers or compositions administered once a day or twice a day have about 85% or more tolerability as the same polymer or composition of the same daily amount administered three times a day. It is also a feature of this invention that the cation exchange polymers or compositions administered once a day or twice a day have about 95% or more tolerability as the same polymer or composition of the same daily amount administered three times a day. It is also a feature of this invention that the cation exchange polymers or compositions administered once a day or twice a day have about substantially the same tolerability as the same polymer or composition of the same daily amount administered three times a day.

When administration is well tolerated, there should be little or no significant dose modification or dose discontinuation by the subject. In some embodiments, well tolerated means there is no apparent dose response relationship for gastrointestinal adverse events. In some of these embodiments, well tolerated means that the following gastrointestinal adverse effects are not reported from a statistically significant number of subjects, including those effects selected from the group consisting of flatulence, diarrhea, abdominal pain, constipation, stomatitis, nausea and vomiting. In particular, the examples also show that there were no severe gastrointestinal adverse events in subjects.

In other embodiments, the present invention provides a method of removing potassium from the gastrointestinal tract of an animal subject in need thereof, comprising administering an effective amount of a crosslinked cation exchange polymer or a composition comprising a crosslinked cation exchange polymer and a linear polyol once per day or twice per day to the subject, wherein the polymer or composition is as well tolerated as administering substantially the same amount of the same polymer or composition three times per day. In some instances, the subject is experiencing hyperkalemia and thus the method treats hyperkalemia. In other instances, the method lowers serum potassium. In particular embodiments, the potassium polymer is a crosslinked aliphatic carboxylic polymer.

The compositions and/or methods of this invention include a composition comprising a crosslinked cation exchange polymer and an effective amount or from about 10 wt. % to about 40 wt. % linear polyol that extracts from an animal subject in need thereof about 5% more potassium as compared to the same dose and same administration frequency of the same composition that does not contain the linear polyol. More specifically, the compositions and/or methods include a composition of the invention that extracts from an animal subject in need thereof about 10% more potassium as compared to the same dose and same administration frequency of the same composition that does not contain the linear polyol. And even more specifically, the compositions and/or methods include a composition of the invention that extracts from an animal subject in need thereof about 15% or about 20% more potassium as compared to the same dose and same administration frequency of the otherwise same composition that does not include the linear polyol.

As shown in the examples, volunteers receiving a composition comprising a calcium salt of crosslinked poly-alpha-fluoroacrylic acid and from about 10 wt. % to about 40 wt. % of a linear polyol once per day excreted 82.8% of the amount of fecal potassium as those volunteers who received substantially the same amount of the same polymer three-times per day. It is also shown that volunteers receiving a composition comprising a calcium salt of cross-linked poly-alpha-fluoroacrylic acid and from about 10 wt. % to about 40 wt. % of a linear polyol twice per day excreted 91.5% of the amount of fecal potassium as those volunteers who received substantially the same amount of the same polymer three-times per day. Fecal excretion is an in vivo measure of efficacy that relates to the lowering of serum potassium in subjects in need thereof.

These results were not based on administration with meals nor were they based on any particular formulation. In particular, the potassium binding polymers or compositions of this invention are substantially unreactive with food and can be added to typical food products (e.g., water, pudding, apple sauce, baked goods, etc.), which adds to compliance enhancement (particularly for patients who are on a water restricted diet). Substantially unreactive in this context means that the polymers or compositions do not effectively change the taste, consistency or other noticeable properties of the food in which it is mixed or placed. Also, the polymers or compositions of this invention can be administered without regard to mealtime. In fact, since potassium being bound is not just from meals, but is potassium that is excreted into the gastrointestinal tract, administration can take place at any time. Dosing regimens also take into account the other embodiments discussed herein, including capacity, amount and form.

If necessary, the crosslinked cation exchange polymers or compositions comprising a crosslinked cation exchange polymer and a linear polyol may be administered in combination with other therapeutic agents. The choice of therapeutic agents that can be co-administered with the compounds of the invention will depend, in part, on the condition being treated.

Further, patients suffering from chronic kidney disease and/or congestive heart failure can be particularly in need of potassium removal because agents used to treat these conditions may cause potassium retention in a significant population of these patients. For these patients, decreased renal potassium excretion results from renal failure (especially with decreased glomerular filtration rate), often coupled with the ingestion of drugs that interfere with potassium excretion, e.g., potassium-sparing diuretics, angiotensin-converting enzyme inhibitors (ACEs), angiotensin receptor blockers (ARBs), beta blockers, renin inhibitors, aldosterone synthase inhibitors, non-steroidal anti-inflammatory drugs, heparin, or trimethoprim. For example, patients suffering from chronic kidney disease can be prescribed various agents that will slow the progression of the disease; for this purpose, angiotensin-converting enzyme inhibitors (ACEs), angiotensin receptor blockers (ARBs), and aldosterone antagonists are commonly prescribed. In these treatment regimens the angiotensin-converting enzyme inhibitor is captopril, zofenopril, enalapril, ramipril, quinapril, perindopril, lisinopril, benazipril, fosinopril, or combinations thereof and the angiotensin receptor blocker is candesartan, eprosartan, irbesartan, losartan, olmesartan, telmisartan, valsartan, or combinations thereof and the renin inhibitor is aliskiren. The aldosterone antagonists can also cause potassium retention. Thus, it can be advantageous for patients in need of these treatments to also be treated with an agent that removes potassium from the body. The aldosterone antagonists typically prescribed are spironolactone, eplerenone, and the like.

In certain particular embodiments, the crosslinked cation exchange polymers or compositions described herein can be administered on a periodic basis to treat a chronic condition. Typically, such treatments will enable patients to continue using drugs that may cause hyperkalemia, such as potassium-sparing diuretics, ACEs, ARBs, aldosterone antagonists, β-blockers, renin inhibitors, non-steroidal anti-inflammatory drugs, heparin, trimethoprim, or combinations thereof. Also, use of the polymeric compositions described herein will enable certain patient populations, who were unable to use certain above-described drugs, to use such drugs.

In certain use situations, the crosslinked cation exchange polymers used are those that are capable of removing less than about 5 mEq of potassium per day, or in the range of about 5 mEq to about 60 mEq of potassium per day.

In certain other embodiments, the compositions and methods described herein are used in the treatment of hyperkalemia in patients in need thereof, for example, when caused by excessive intake of potassium. Excessive potassium intake alone is an uncommon cause of hyperkalemia. More often, hyperkalemia is caused by indiscriminate potassium consumption in a patient with impaired mechanisms for the intracellular shift of potassium or renal potassium excretion.

In the present invention, the crosslinked cation exchange polymers or compositions comprising a crosslinked cation exchange polymer and a linear polyol can be co-administered with other active pharmaceutical agents. This co-administration can include simultaneous administration of the two agents in the same dosage form, simultaneous administration in separate dosage forms, and separate administration. For example, for the treatment of hyperkalemia, the crosslinked cation exchange polymer or composition of the invention can be co-administered with drugs that cause the hyperkalemia, such as potassium-sparing diuretics, angiotensin-converting enzyme inhibitors (ACEs), angiotensin receptor blockers (ARBs), beta blockers, renin inhibitors, non-steroidal anti-inflammatory drugs, heparin, or trimethoprim. In particular, the crosslinked cation exchange polymer or composition can be co-administered with ACEs (e.g., captopril, zofenopril, enalapril, ramipril, quinapril, perindopril, lisinopril, benazipril, and fosinopril), ARBs (e.g., candesartan, eprosartan, irbesartan, losartan, olmesartan, telmisartan, and valsartan) and renin inhibitors (e.g. aliskiren). In particular embodiments, the agents are simultaneously administered, wherein both the agents are present in separate compositions. In other embodiments, the agents are administered separately in time (i.e., sequentially).

The term "treating" as used herein includes achieving a therapeutic benefit. By therapeutic benefit is meant eradication, amelioration, or prevention of the underlying disorder being treated. For example, in a hyperkalemia patient, therapeutic benefit includes eradication or amelioration of the underlying hyperkalemia. Also, a therapeutic benefit is achieved with the eradication, amelioration, or prevention of one or more of the physiological symptoms associated with the underlying disorder such that an improvement is observed in the patient, notwithstanding that the patient may still be afflicted with the underlying disorder. For example, administration of a potassium-binding polymer to a patient experiencing hyperkalemia provides therapeutic benefit not only when the patient's serum potassium level is decreased, but also when an improvement is observed in the patient with respect to other disorders that accompany hyperkalemia, like renal failure. In some treatment regimens, the crosslinked cation exchange polymer or composition of the invention may be administered to a patient at risk of developing hyperkalemia or to a patient reporting one or more of the physiological symptoms of hyperkalemia, even though a diagnosis of hyperkalemia may not have been made.

The pharmaceutical compositions of the present invention include compositions wherein the crosslinked cation exchange polymers are present in an effective amount, i.e., in an amount effective to achieve therapeutic or prophylactic benefit. The actual amount effective for a particular application will depend on the patient (e.g., age, weight, etc.), the condition being treated, and the route of administration. Determination of an effective amount is well within the capabilities of those skilled in the art, especially in light of the disclosure herein. The effective amount for use in humans can be determined from animal models. For example, a dose for humans can be formulated to achieve gastrointestinal concentrations that have been found to be effective in animals.

The polymers and compositions described herein can be used as food products and/or food additives. They can be added to foods prior to consumption or while packaging. The polymers and compositions can also be used in fodder for animals to lower potassium levels, which is desirable in fodders for pigs and poultry to lower the water secretion.

The crosslinked cation exchange polymers or pharmaceutically acceptable salts thereof, or compositions described herein, can be delivered to the patient using a wide variety of routes or modes of administration. The most preferred routes for administration are oral, intestinal, or rectal. Rectal routes of administration are known to those of skill in the art. Intestinal routes of administration generally refer to administration directly into a segment of the gastrointestinal tract, e.g., through a gastrointestinal tube or through a stoma. The most preferred route for administration is oral.

The polymers (or pharmaceutically acceptable salts thereof) may be administered per se or in the form of a pharmaceutical composition wherein the active compound(s) is in admixture or mixture with one or more pharmaceutically acceptable excipients. Pharmaceutical compositions for use in accordance with the present invention may be formulated in conventional manner using one or more pharmaceutically acceptable excipients comprising carriers, diluents, and auxiliaries which facilitate processing of the active compounds into preparations which can be used physiologically. Proper composition is dependent upon the route of administration chosen.

For oral administration, the polymers or compositions of the invention can be formulated readily by combining the polymer or composition with pharmaceutically acceptable excipients well known in the art. Such excipients enable the compositions of the invention to be formulated as tablets, pills, dragees, capsules, liquids, gels, syrups, slurries, suspensions, wafers, and the like, for oral ingestion by a patient to be treated. In one embodiment, the oral composition does not have an enteric coating. Pharmaceutical preparations for oral use can be obtained as a solid excipient, optionally grinding a resulting mixture, and processing the mixture of granules, after adding suitable auxiliaries, if desired, to obtain tablets or dragee cores. Suitable excipients are, in particular, fillers such as sugars, including lactose or sucrose; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinyl pyrrolidone (PVP); and various flavoring agents known in the art. If desired, disintegrating agents may be added, such as the cross-linked polyvinyl pyrrolidone, agar, or alginic acid or a salt thereof such as sodium alginate.

In various embodiments, the active ingredient (e.g., polymer) constitutes over about 20%, more particularly over about 40%, even more particularly over about 50%, and most particularly more than about 60% by weight of the oral dosage form, the remainder comprising suitable excipient(s). In compositions containing water and linear polyol, the polymer preferably constitutes over about 20%, more particularly over about 40%, and even more particularly over about 50% by weight of the oral dosage form.

In some embodiments, pharmaceutical compositions are in the form of liquid compositions. In various embodiments, the pharmaceutical composition contains a crosslinked cation exchange polymer dispersed in a suitable liquid excipient. Suitable liquid excipients are known in the art; see, e.g., Remington's Pharmaceutical Sciences.

Unless otherwise indicated, an alkyl group as described herein alone or as part of another group is an optionally substituted linear saturated monovalent hydrocarbon radical containing from one to twenty carbon atoms and preferably one to eight carbon atoms, or an optionally substituted branched saturated monovalent hydrocarbon radical containing three to twenty carbon atoms, and preferably three to eight carbon atoms. Examples of unsubstituted alkyl groups include methyl, ethyl, n-propyl, i-propyl, n-butyl, i-butyl, s-butyl, t-butyl, n-pentyl, i-pentyl, s-pentyl, t-pentyl, and the like.

The term "amide moiety" as used herein represents a bivalent (i.e., difunctional) group including at least one amido linkage

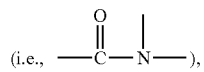

such as —C(O)—NR$_A$—R$_C$—NR$_B$—C(O)— wherein R$_A$ and R$_B$ are independently hydrogen or alkyl and R$_C$ is alkylene. For example, an amide moiety can be —C(O)—NH—(CH$_2$)$_p$—NH—C(O)— wherein p is an integer of 1 to 8.

The term "aryl" as used herein alone or as part of another group denotes an optionally substituted monovalent aromatic hydrocarbon radical, preferably a monovalent monocyclic or bicyclic group containing from 6 to 12 carbons in the ring portion, such as phenyl, biphenyl, naphthyl, substituted phenyl, substituted biphenyl or substituted naphthyl. Phenyl and substituted phenyl are the more preferred aryl groups. The term "aryl" also includes heteroaryl.

The terms "carboxylic acid group", "carboxylic" or "carboxyl" denote the monovalent radical —C(O)OH. Depending upon the pH conditions, the monovalent radical can be in the form —C(O)O$^-$Q$^+$ wherein Q$^+$ is a cation (e.g., sodium), or two of the monovalent radicals in close proximity can bond with a divalent cation Q$^{2+}$ (e.g., calcium, magnesium), or a combination of these monovalent radicals and —C(O)OH are present.

The term "cycloalkyl" as used herein denotes optionally an optionally substituted cyclic saturated monovalent bridged or non-bridged hydrocarbon radical containing from three to eight carbon atoms in one ring and up to 20 carbon atoms in a multiple ring group. Exemplary unsubstituted cycloalkyl groups include cyclopropyl, cyclobutyl, cyclopentyl, cyclohexyl, cycloheptyl, cyclooctyl, adamantyl, norbornyl, and the like.

The term "-ene" as used as a suffix as part of another group denotes a bivalent radical in which a hydrogen atom is removed from each of two terminal carbons of the group, or if the group is cyclic, from each of two different carbon atoms in the ring. For example, alkylene denotes a bivalent alkyl group such as methylene (—CH$_2$—) or ethylene (—CH$_2$CH$_2$—), and arylene denotes a bivalent aryl group such as o-phenylene, m-phenylene, or p-phenylene.

The term "ether moiety" as used herein represents a bivalent (i.e., difunctional) group including at least one ether linkage (i.e., —O—). For example, in Formulae 3 or 33 as defined herein, the ether moiety can be —R$_A$OR$_B$— or —R$_A$OR$_C$OR$_B$— wherein R$_A$, R$_B$ and R$_C$ are independently alkylene.

The term "heteroaryl," as used herein alone or as part of another group, denotes an optionally substituted monovalent monocyclic or bicyclic aromatic radical of 5 to 10 ring atoms, where one or more, preferably one, two, or three, ring atoms are heteroatoms independently selected from N, O, and S, and the remaining ring atoms are carbon. Exemplary heteroaryl moieties include benzofuranyl, benzo[d]thiazolyl, isoquinolinyl, quinolinyl, thiophenyl, imidazolyl, oxazolyl, quinolinyl, furanyl, thazolyl, pyridinyl, furyl, thienyl, pyridyl, oxazolyl, pyrrolyl, indolyl, quinolinyl, isoquinolinyl, and the like.

The term "heterocyclo," as used herein alone or as part of another group, denotes a saturated or unsaturated monovalent monocyclic group of 4 to 8 ring atoms, in which one or two ring atoms are heteroatom(s), independently selected from N, O, and S, and the remaining ring atoms are carbon atoms. Additionally, the heterocyclic ring may be fused to a phenyl or heteroaryl ring, provided that the entire heterocyclic ring is not completely aromatic. Exemplary heterocyclo groups include the heteroaryl groups described above, pyrrolidino, piperidino, morpholino, piperazino, and the like.

The term "hydrocarbon" as used herein describes a compound or radical consisting exclusively of the elements carbon and hydrogen.

The term "phosphonic" or "phosphonyl" denotes the monovalent radical

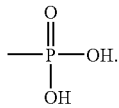

The term "phosphoric" or "phosphoryl" denotes the monovalent radical

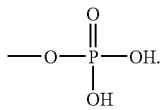

The term "protected" as used herein as part of another group denotes a group that blocks reaction at the protected portion of a compound while being easily removed under conditions that are sufficiently mild so as not to disturb other substituents of the compound. For example, a protected carboxylic acid group-C(O)OP$_g$ or a protected phosphoric acid group —OP(O)(OH)OP$_g$ or a protected phosphonic acid group —P(O)(OH)OP$_g$ each have a protecting group P$_g$ associated with the oxygen of the acid group wherein P$_g$ can be alkyl (e.g., methyl, ethyl, n-propyl, i-propyl, n-butyl, i-butyl, s-butyl, t-butyl, n-pentyl, i-pentyl, s-pentyl, t-pentyl, and the like), benzyl, silyl (e.g., trimethylsilyl (TMS), triethylsilyl (TES), triisopropylsilyl (TIPS), triphenylsilyl (TPS), t-butyldimethylsilyl (TBDMS), t-butyldiphenylsilyl (TBDPS) and the like. A variety of protecting groups and the synthesis thereof may be found in "Protective Groups in Organic Synthesis" by T. W. Greene and P. G. M. Wuts, John Wiley & Sons, 1999. When the term "protected" introduces a list of possible protected groups, it is intended that the term apply to every member of that group. That is, the phrase "protected carboxylic, phosphonic or phosphoric" is to be interpreted as "protected carboxylic, protected phosphonic or protected phosphoric." Likewise, the phrase "optionally protected carboxylic, phosphoric or phosphonic" is to be interpreted as "optionally protected carboxylic, optionally protected phosphonic or optionally protected phosphoric."

The term "substituted" as in "substituted aryl," "substituted alkyl," and the like, means that in the group in question (i.e., the alkyl, aryl or other group that follows the term), at least one hydrogen atom bound to a carbon atom is replaced with one or more substituent groups such as hydroxy (—OH), alkylthio, phosphino, amido (—CON(R$_A$)(R$_B$), wherein R$_A$ and R$_B$ are independently hydrogen, alkyl, or aryl), amino(—N(R$_A$)(R$_B$), wherein R$_A$ and R$_B$ are independently hydrogen, alkyl or aryl), halo (fluoro, chloro, bromo, or iodo), silyl, nitro (—NO$_2$), an ether (—OR$_A$ wherein R$_A$ is alkyl or aryl), an ester (—OC(O)R$_A$ wherein R$_A$ is alkyl or aryl), keto (—C(O)R$_A$ wherein R$_A$ is alkyl or aryl), heterocyclo, and the like. When the term "substituted" introduces a list of possible substituted groups, it is intended that the term apply to every member of that group. That is, the phrase "optionally substituted alkyl or aryl" is to be interpreted as "optionally substituted alkyl or optionally substituted aryl."

Having described the invention in detail, it will be apparent that modifications and variations are possible without departing from the scope of the invention defined in the appended claims.

EXAMPLES

The following non-limiting examples are provided to further illustrate the present invention.

Materials for Examples 1-5

Methyl 2-fluoroacrylate (MeFA; SynQuest Labs) contained 0.2 wt % hydroquinone and was vacuum distilled before use. Divinylbenzene (DVB; Aldrich) was technical grade, 80%, mixture of isomers. 1,7-octadiene (ODE 98%; Aldrich), lauroyl peroxide (LPO 99%; ACROS Organics), polyvinyl alcohol (PVA typical molecular weight 85,000-146,000, 87-89% hydrolyzed; Aldrich), sodium chloride (NaCl; Aldrich), sodium phosphate dibasic heptahydrate (Na$_2$HPO$_4$.7H$_2$O; Aldrich), and sodium phosphate monobasic monohydrate (NaH$_2$PO$_4$.H$_2$O; Aldrich) were used as received.

Example 1

DVB as Crosslinking Monomer

The polymerization was carried out in a 1 L three-neck Morton-type round bottom flask equipped with an overhead mechanical stirrer with a Teflon paddle and a water condenser. An organic phase was prepared by mixing MeFA (54 g), DVB (6 g) and LPO (0.6 g), and an aqueous phase was prepared by dissolving PVA (3 g) and NaCl (11.25 g) in water (285.75 g). The organic and aqueous phases were then mixed in the flask and stirred at 300 rpm under nitrogen. The flask was immersed in a 70° C. oil bath for 3 hours, and cooled to room temperature. The internal temperature during the reaction was about 65° C. The solid product was washed with water and collected by decanting off supernatant solution. The white solid was freeze-dried, affording dry solid polyMeFA particles (or beads) (56.15 g, 94%).

Hydrolysis was carried out in the same setup as for the polymerization. PolyMeFA particles (48.93 g) from above were suspended in KOH solution (500 g, 10 wt. %) and stirred at 300 rpm. The mixture was heated in a 95° C. oil bath for 20 hours and cooled to room temperature. The solid product was washed with water and collected by decanting off the supernatant solution. After freeze-drying, poly fluoroacrylic acid (polyFAA) particles (48.54 g, 82%) were obtained. These particles were in the form of beads.

Example 2

Polymer Synthesis Using Two Crosslinking Monomers

Multiple suspension polymerizations were carried out in a manner substantially similar to Example 1. The synthesis conditions and results are summarized in Table 1. Compared to Example 1, the addition of ODE as a second crosslinker in all ratios tested increased the yield after the hydrolysis step. Therefore the overall yield for polyFAA bead synthesis was improved to a level of greater than 90%.

TABLE 1

Synthesis conditions and selected properties

| | | | Aqueous Phase | | Organic Phase | | | | | | | |
| | | | pH | | | | | | Yield | | Swelling | BC |
| | | | before | H after | MeFA | DVB | ODE | | | | | |
| Exp # | Buffer | NaCl | polymz | polymz | wt. % | wt. % | wt. % | Susp. | Hydro. | Overall | Ratio | mmol/g |
|---|---|---|---|---|---|---|---|---|---|---|---|---|
| Comp 1 | no | 3.75% | nm | 4.00 | 95 | 5 | 0 | 98% | 64% | 63% | 2.66 | 9.59 |
| Comp 2 | no | 3.75% | nm | 3.90 | 90 | 10 | 0 | 94% | 82% | 77% | 1.52 | 8.72 |
| Comp 3 | no | 3.75% | nm | 3.50 | 80 | 20 | 0 | 89% | 90% | 80% | 1.01 | 5.96 |
| Ex 789 | no | 3.75% | 5.10 | 3.50 | 90 | 8 | 2 | 95% | 100% | 95% | 1.58 | 8.70 |
| Ex 792 | 0.25% | 3.50% | 8.30 | 3.95 | | | | 94% | 100% | 94% | 1.49 | 8.76 |
| Ex 793 | 0.50% | 3.25% | 8.45 | 5.28 | | | | 94% | 95% | 89% | 1.44 | 8.62 |
| Ex 808 | 0.50% | 3.25% | nm | nm | | | | nm | nm | 92% | nm | 8.76 |
| Ex 811 | 0.50% | 3.25% | 7.25 | 5.05 | | | | nm | nm | 93% | nm | nm |
| Ex 815 | 0.75% | 2.50% | 7.24 | 5.26 | | | | nm | nm | 88% | nm | nm |
| Ex 816 | 0.75% | 2.50% | 7.16 | 4.62 | | | | 87% | 94% | 82% | nm | nm |
| Ex 814 | 1.00% | 0.00% | 7.66 | 5.51 | | | | | aggregates | | nm | nm |
| Ex 794 | no | 3.75% | 5.78 | nm | 90 | 5 | 5 | 95% | 100% | 95% | 1.57 | 9.26 |
| Ex 803 | no | 3.75% | 5.17 | 3.94 | | | | nm | nm | 95% | 1.44 | 8.70 |
| Ex 805 | 0.50% | 3.25% | 7.00 | 5.23 | | | | nm | nm | 95% | 1.51 | 8.70 |
| Ex 812 | 0.50% | 3.25% | 7.29 | 5.21 | | | | nm | nm | 95% | nm | nm |
| Ex 801 | no | 3.75% | 5.18 | 3.11 | 90 | 2 | 8 | 93% | 100% | 93% | 1.80 | 9.05 |
| Ex 806 | 0.50% | 3.25% | 7.00 | 5.44 | | | | nm | nm | 94% | 1.67 | 8.21 |
| Ex 796 | no | 3.75% | nm | nm | 90 | 0 | 10 | 87% | 98% | 85% | 2.34 | 9.87 |
| Ex 800 | 0.50% | 3.25% | 8.24 | 4.93 | 90 | 0 | 10 | 92% | 95% | 87% | 2.51 | 9.46 |
| Ex 802 | 0.50% | 3.25% | 8.27 | 5.44 | 85 | 0 | 15 | 88% | 95% | 84% | 2.33 | 8.98 |

Note:
(1) buffer, $Na_2HPO_4/NaH_2PO_4$;
(2) swelling ratio, measured using salt form;
(3) BC, binding capacity, measured using H form in 100 mM KOH solution;
(4) In Ex 816, 200 ppm $NaNO_2$ was added in aqueous phase;
(5) nm, means not measured;
(6) polymz means polymerization;
(7) Susp. means suspension;
(8) Hydro. means hydrolysis.

Examples 3-5

Synthesis of FAA Beads With DVB/ODE

The polymers of examples 3-5 were prepared as follows. A polymerization was carried out in a 1 L three-neck Morton-type round bottom flask equipped with an overhead mechanical stirrer with a Teflon paddle and a water condenser. An organic phase was prepared by mixing MeFA, DVB, ODE and LPO (0.6 g), and an aqueous phase was prepared by dissolving PVA (3 g) and NaCl (11.25 g) in water (285.75 g). The organic and aqueous phases were then mixed in the flask, and stirred at 300 rpm under nitrogen. The flask was immersed in a 70° C. oil bath for 5 hours, and cooled to room temperature. The internal temperature during reaction was about 65° C. The solid product was washed with water and collected by filtration. The white solid was freeze-dried, affording dry solid polyMeFA beads.

Hydrolysis was carried out in the same setup as for the polymerization. PolyMeFA beads from the polymerization reaction were suspended in a NaOH solution (400 g, 10 wt %) and stirred at 200 rpm. The mixture was heated in a 95° C. oil bath for 20 hours and cooled to room temperature. The solid product was washed with water and collected by filtration. After freeze-drying, polyFAA beads were obtained. The synthesis conditions and selected properties are summarized below:

| | Organic Phase | | | | | | Hydrolysis | Yield | |
|---|---|---|---|---|---|---|---|---|---|
| Exm # | MeFA (g) | DVB (g) | ODE (g) | MeFA wt. % | DVB wt. | ODE wt. | polyMeFA (g) | Susp. (g), % | Hydro. (g), % |
| 3 | 54 | 4.8 | 1.2 | 90 | 8 | 2 | 40.26 | 56.74, 95% | 43.16, 100% |
| 4 | 54 | 3 | 3 | 90 | 5 | 5 | 39.17 | 56.91, 95% | 42.31, 100% |
| 5 | 54 | 1.2 | 4.8 | 90 | 2 | 8 | 38.23 | 55.94, 93% | 41.62, 100% |

The calcium form of the polyFAA beads of Example 4 was prepared by exposing the (sodium 2-fluoroacrylate)-divinylbenzene-1,7-octadiene copolymer to an excess of aqueous calcium chloride solution to yield insoluble cross-linked (calcium 2-fluoroacrylate)-divinylbenzene-1,7-octadiene copolymer. After the calcium ion exchange, the Ca(polyFAA) final product was washed with ethanol and water.

Example 6

Preparation of Compositions with Ca(polyFAA) and Stabilizing Polyol and Stability Testing of Such Compositions During Storage Composition Preparation: To a 500 mL 3-necked round bottom flask equipped with a magnetic stirrer and nitrogen inlet adapter was charged D-sorbitol (60 g; 0.3 moles) followed by 240 g of water. The mixture was stirred until a clear solution was obtained. Ca(polyFAA) (30 g) prepared by the process described in Example 4 was added in one portion to the sorbitol solution and the resultant slurry was stirred at ambient temperature (20-25° C.) for three hours. The solids were filtered off and dried under reduced pressure to the desired water content. The solids (35.1 g) were analyzed for sugar alcohol content, loss on drying (LOD), and calcium content. This same sample preparation technique was used for the other compositions, with the specific details of varying D-sorbitol concentrations, times of mixing and drying as set forth in Table 2.

The samples prepared as discussed above were placed in storage at the temperatures and times listed in Tables 3-12. For the samples stored at 5° C. and ambient temperature, the samples were transferred to a vial, which was placed in a Sure-Seal bag and sealed, and then placed in a second Sure-Seal bag with a desiccant (calcium sulfate) in the second bag, which was also sealed. For the samples at higher temperatures, the samples were placed in vials and stored at the stated temperatures. At the specified time (1 week, 3 weeks, 5 weeks, 7 weeks, etc.), aliquots of the samples were removed from storage and tested for their weight, moisture content, LOD and free inorganic fluoride. These tests were carried out as detailed in the specification above. Fluoride concentrations shown in Tables 6A to 6J below have been corrected for water and polyol weight.

TABLE 2

| Example No. | SORBITOL CONCENTRATION USED FOR LOADING (W/W %) | SORBITOL LOADING (W/W %) | MIXING TIME | DRYING METHOD |
|---|---|---|---|---|
| 6A | 2 | 3.1 | 1.5 h | lyophilization |
| 6B | 5 | 7.3 | 3 h | lyophilization |
| 6C | 10 | 12.3 | 3 h | lyophilization |
| 6D | 20 | 17.2 | 3 h | lyophilization |
| 6E | 20 | 18.3 | 3 h | air dried under vacuum |
| 6F | 20 | 18.3 | 3 h | lyophilization |
| 6G | 30 | 22.5 | 1.5 h | air dried under vacuum |
| 6H | 30 | 22.5 | 3 h | lyophilization |
| 6I | 45 | 24.9 | 3 h | air dried under vacuum |
| 6J | 45 | 24.9 | 1.5 h | lyophilization |

TABLE 3

Sample 6A

| TIME POINT | STORAGE CONDITIONS | Sample Weight (g) | Moisture Content (%) | Sample Dry Weight (g) | Fluoride Reading (ppm) | Fluoride Conc. (ug/g) |
|---|---|---|---|---|---|---|
| T = 0 | 5-8° C. | 0.498 | 4.80 | 0.474 | 2.79 | 607 |
|  | 20-25° C. |  |  |  |  |  |
|  | 40° C. |  |  |  |  |  |
| T = 1 WEEK | 5-8° C. | 0.496 | 5.72 | 0.468 | 3.04 | 671 |
|  | 20-25° C. | 0.504 | 6.00 | 0.474 | 4.53 | 987 |
|  | 40° C. | 0.545 | 5.48 | 0.515 | 9.79 | 1961 |
| T = 3 WEEKS | 5-8° C. | 0.508 | 4.99 | 0.483 | 3.53 | 754 |
|  | 20-25° C. | 0.505 | 4.97 | 0.480 | 6.28 | 1351 |
|  | 40° C. | n/a | n/a | n/a | n/a | n/a |
| T = 5 WEEKS | 5-8° C. | 0.315 | 8.06 | 0.290 | 4.69 | 1003 |
|  | 20-25° C. | 0.317 | 6.03 | 0.298 | 7.33 | 1523 |
|  | 40° C. | n/a | n/a | n/a | n/a | n/a |
| T = 7 WEEKS | 5-8° C. | 0.513 | 8.06 | 0.472 | 4.6 | 1006 |
|  | 20-25° C. | 0.513 | 6.03 | 0.482 | 7.63 | 607 |
|  | 40° C. | n/a | n/a | n/a | n/a | n/a |

TABLE 4

Sample 6B

| TIME POINT | STORAGE CONDITIONS | Sample Weight (g) | Moisture Content (%) | Sample Dry Weight (g) | Fluoride Reading (ppm) | Fluoride Conc (ug/g) |
|---|---|---|---|---|---|---|
| T = 0 | 5-8° C. | 0.514 | 5.34 | 0.487 | 1.74 | 385 |
|  | 20-25° C. |  |  |  |  |  |
|  | 40° C. |  |  |  |  |  |
| T = 1 WEEK | 5-8° C. | 0.537 | 6.31 | 0.503 | 1.99 | 427 |
|  | 20-25° C. | 0.518 | 6.57 | 0.484 | 3.08 | 686 |
|  | 40° C. | 0.52 | 7.03 | 0.483 | 7.03 | 1569 |
| T = 3 WEEKS | 5-8° C. | 0.513 | 5.21 | 0.486 | 2.15 | 477 |
|  | 20-25° C. | 0.501 | 6.07 | 0.471 | 4.3 | 986 |
|  | 40° C. | n/a | n/a | n/a | n/a | n/a |
| T = 5 | 5-8° C. | 0.5031 | 5.97 | 0.473 | 2.77 | 632 |

TABLE 4-continued

Sample 6B

| TIME POINT | STORAGE CONDITIONS | Sample Weight (g) | Moisture Content (%) | Sample Dry Weight (g) | Fluoride Reading (ppm) | Fluoride Conc (ug/g) |
|---|---|---|---|---|---|---|
| WEEKS | 20-25° C. | 0.5092 | 6.79 | 0.475 | 5.17 | 1175 |
|  | 40° C. | n/a | n/a | n/a | n/a | n/a |
| T = 7 | 5-8° C. | 0.507 | 5.97 | 0.477 | 2.76 | 625 |
| WEEKS | 20-25° C. | 0.508 | 6.79 | 0.474 | 5.67 | 1291 |
|  | 40° C. | n/a | n/a | n/a | n/a | n/a |
| T = 9 | 5-8° C. | 0.504 | 5.97 | 0.474 | 2.81 | 640 |
| WEEKS | 20-25° C. | n/a | n/a | n/a | n/a | n/a |
|  | 40° C. | n/a | n/a | n/a | n/a | n/a |

TABLE 5

Sample 6C

| TIME POINT | STORAGE CONDITIONS | Sample Weight (g) | Moisture Content (%) | Sample Dry Weight (g) | Fluoride Reading (ppm) | Fluoride Conc (ug/g) |
|---|---|---|---|---|---|---|
| T = 0 | 5-8° C. | 0.512 | 5.98 | 0.481 | 1.1 | 228.7 |
|  | 20-25° C. |  |  |  |  |  |
|  | 40° C. |  |  |  |  |  |
| T = 1 | 5-8° C. | 0.576 | 5.98 | 0.542 | 1.28 | 269 |
| WEEK | 20-25° C. | 0.506 | 5.71 | 0.477 | 1.88 | 449 |
|  | 40° C. | 0.52 | 5.63 | 0.491 | 4.61 | 1071 |
| T = 3 | 5-8° C. | 0.527 | 6.86 | 0.491 | 1.3 | 302 |
| WEEKS | 20-25° C. | 0.512 | 6.56 | 0.478 | 2.46 | 586 |
|  | 40° C. | 0.506 | 6.74 | 0.472 | 6.44 | 1556 |
| T = 5 | 5-8° C. | 0.5104 | 7.19 | 0.474 | 1.80 | 433 |
| WEEKS | 20-25° C. | 0.5118 | 6.95 | 0.476 | 3.29 | 788 |
|  | 40° C. | n/a | n/a | n/a | n/a | n/a |
| T = 7 | 5-8° C. | 0.513 | 7.19 | 0.476 | 1.75 | 420 |
| WEEKS | 20-25° C. | 0.521 | 6.95 | 0.485 | 3.4 | 799 |
|  | 40° C. | 0.508 | 6.74 | 0.474 | 7.84 | 1887 |
| T = 9 | 5-8° C. | 0.527 | 7.19 | 0.489 | 1.81 | 422 |
| WEEKS | 20-25° C. | n/a | n/a | n/a | n/a | n/a |
|  | 40° C. | n/a | n/a | n/a | n/a | n/a |

TABLE 6

Sample 6D

| TIME POINT | STORAGE CONDITIONS | Sample Weight (g) | Moisture Content (%) | Sample Dry Weight (g) | Fluoride Reading (ppm) | Fluoride Conc. (ug/g) |
|---|---|---|---|---|---|---|
| T = 0 | 5-8° C. | 0.517 | 7.41 | 0.479 | 0.5 | 126 |
|  | 20-25° C. |  |  |  |  |  |
|  | 40° C. |  |  |  |  |  |
| T = 1 | 5-8° C. | 0.503 | 7.52 | 0.465 | 0.649 | 169 |
| WEEK | 20-25° C. | 0.534 | 8.2 | 0.490 | 1.03 | 254 |
|  | 40° C. | 0.562 | 6.95 | 0.523 | 2.55 | 589 |
| T = 3 | 5-8° C. | 0.525 | 6.73 | 0.490 | 0.659 | 163 |
| WEEKS | 20-25° C. | 0.524 | 6.91 | 0.488 | 1.2 | 297 |
|  | 40° C. | 0.514 | 6.63 | 0.480 | 2.75 | 692 |
| T = 5 | 5-8° C. | 0.5157 | 7.08 | 0.479 | 0.819 | 207 |
| WEEKS | 20-25° C. | 0.5062 | 7.56 | 0.468 | 1.47 | 379 |
|  | 40° C. | 0.5416 | 8.8 | 0.494 | 4.15 | 1014 |
| T = 7 | 5-8° C. | 0.525 | 7.08 | 0.488 | 0.809 | 200 |
| WEEKS | 20-25° C. | 0.519 | 7.56 | 0.480 | 1.65 | 415 |
|  | 40° C. | 0.524 | 8.8 | 0.478 | 4.56 | 1152 |
| T = 9 | 5-8° C. | 0.513 | 7.56 | 0.474 | 0.734 | 187 |
| WEEKS | 20-25° C. | n/a | n/a | n/a | n/a | n/a |
|  | 40° C. | n/a | n/a | n/a | n/a | n/a |

TABLE 7

Sample 6E

| TIME POINT | STORAGE CONDITIONS | Sample Wt (g) | Moisture Content (%) | Dry Weight (g) | Fluoride Reading (ppm) | Fluoride Conc. (ug/g) |
|---|---|---|---|---|---|---|
| T = 0 | 5-8° C. | 0.55 | 17.00 | 0.457 | 0.05 | 13 |
| | 20-25° C. | | | | | |
| | 40° C. | | | | | |
| T = 2 WEEKS | 5-8° C. | 0.504 | 16.53 | 0.421 | 0.04 | 12 |
| | 20-25° C. | 0.507 | 16.30 | 0.424 | 0.08 | 23 |
| | 40° C. | 0.507 | 16.20 | 0.425 | 0.75 | 217 |
| T = 4 WEEKS | 5-8° C. | 0.519 | 16.60 | 0.433 | 0.04 | 11 |
| | 20-25° C. | 0.508 | 15.60 | 0.429 | 0.09 | 26 |
| | 40° C. | 0.513 | 13.50 | 0.444 | 0.95 | 262 |
| T = 6 WEEKS | 5-8° C. | 0.506 | 15.34 | 0.428 | 0.03 | 9 |
| | 20-25° C. | 0.511 | 15.57 | 0.431 | 0.05 | 15 |
| | 40° C. | 0.507 | 14.72 | 0.432 | 1.35 | 382 |
| T = 8 WEEKS | 5-8° C. | 0.514 | 16.81 | 0.428 | 0.04 | 11 |
| | 20-25° C. | 0.5 | 16.09 | 0.420 | 0.06 | 17 |
| | 40° C. | 0.511 | 14.28 | 0.438 | 1.36 | 379 |
| T = 9 WEEKS | 5-8° C. | 0.509 | 17.11 | 0.422 | 0.05 | 15 |
| | 20-25° C. | 0.502 | 16.00 | 0.422 | 0.28 | 81 |
| | 40° C. | 0.525 | 15.60 | 0.443 | 2.03 | 561 |
| T = 10 WEEKS | 5-8° C. | 0.514 | 17.19 | 0.426 | 0.05 | 15 |
| | 20-25° C. | 0.524 | 15.56 | 0.442 | 0.31 | 86 |
| | 40° C. | 0.502 | 15.10 | 0.426 | 2.2 | 632 |
| T = 12 WEEKS | 5-8° C. | 0.503 | 17.20 | 0.416 | 0.26 | 7 |
| | 20-25° C. | 0.505 | 15.60 | 0.426 | 6.3 | 181 |
| | 40° C. | 0.514 | 15.10 | 0.436 | 2.46 | 690 |

TABLE 8

Sample 6F

| TIME POINT | STORAGE CONDITIONS | Sample Wt (g) | Moisture Content (%) | Sample Dry Weight (g) | Fluoride Reading (ppm) | Fluoride Conc. (ug/g) |
|---|---|---|---|---|---|---|
| T = 0 | 5-8° C. | 0.519 | 6.85 | 0.483 | 0.16 | 39 |
| | 20-25° C. | | | | | |
| | 40° C. | | | | | |
| T = 2 WEEKS | 5-8° C. | 0.504 | 8.08 | 0.463 | 0.15 | 39 |
| | 20-25° C. | 0.557 | 7.78 | 0.514 | 0.58 | 138 |
| | 40° C. | 0.516 | 9.55 | 0.467 | 1.40 | 367 |
| T = 4 WEEKS | 5-8° C. | 0.533 | 8.33 | 0.489 | 0.16 | 40 |
| | 20-25° C. | 0.540 | 7.40 | 0.500 | 0.56 | 137 |
| | 40° C. | 0.510 | 7.50 | 0.472 | 2.25 | 584 |
| T = 6 WEEKS | 5-8° C. | 0.507 | 7.74 | 0.468 | 0.09 | 23 |
| | 20-25° C. | 0.501 | 7.14 | 0.465 | 0.55 | 144 |
| | 40° C. | 0.504 | 7.59 | 0.466 | 2.39 | 628 |
| T = 8 WEEKS | 5-8° C. | 0.503 | 7.88 | 0.463 | 0.08 | 21 |
| | 20-25° C. | 0.502 | 7.54 | 0.464 | 0.53 | 140 |
| | 40° C. | 0.510 | 8.59 | 0.466 | 2.36 | 619 |
| T = 9 WEEKS | 5-8° C. | 0.509 | 7.49 | 0.471 | 0.33 | 86 |
| | 20-25° C. | 0.509 | 7.57 | 0.470 | 1.05 | 273 |
| | 40° C. | 0.492 | 8.04 | 0.452 | 2.61 | 706 |
| T = 10 WEEKS | 5-8° C. | 0.503 | 7.49 | 0.465 | 0.33 | 87 |
| | 20-25° C. | 0.52 | 7.57 | 0.481 | 1.12 | 285 |
| | 40° C. | 0.504 | 8.04 | 0.463 | 3.03 | 800 |
| T = 12 WEEKS | 5-8° C. | 0.502 | 7.49 | 0.464 | 2.48 | 65 |
| | 20-25° C. | 0.504 | 7.57 | 0.466 | 6.82 | 179 |
| | 40° C. | 0.498 | 8.04 | 0.458 | 4.02 | 1075 |

TABLE 9

Sample 6G

| TIME POINT | STORAGE CONDITIONS | Sample Weight (g) | Moisture Content (%) | Sample Dry Weight (g) | Fluoride Reading (ppm) | Fluoride Conc (ug/g) |
|---|---|---|---|---|---|---|
| T = 0 | 5-8° C. | 0.588 | 17.5 | 0.485 | 0.06 | 15 |
| | 20-25° C. | | | | | |
| | 40° C. | | | | | |
| T = 2 WEEKS | 5-8° C. | 0.501 | 16.7 | 0.417 | 0.05 | 15 |
| | 20-25° C. | 0.532 | 16.6 | 0.444 | 0.07 | 21 |
| | 40° C. | 0.509 | 15.8 | 0.429 | 0.54 | 161 |
| T = 4 WEEKS | 5-8° C. | 0.506 | 16.1 | 0.425 | 0.02 | 6 |
| | 20-25° C. | 0.505 | 15.2 | 0.428 | 0.03 | 9 |
| | 40° C. | 0.523 | 15.1 | 0.444 | 0.613 | 178 |
| T = 6 WEEKS | 5-8° C. | 0.502 | 15.62 | 0.424 | 0.02 | 6 |
| | 20-25° C. | 0.501 | 14.39 | 0.429 | 0.04 | 12 |
| | 40° C. | 0.517 | 14.28 | 0.443 | 1.11 | 323 |
| T = 8 WEEKS | 5-8° C. | 0.515 | 16.32 | 0.431 | 0.04 | 12 |
| | 20-25° C. | 0.512 | 15.95 | 0.430 | 0.04 | 12 |
| | 40° C. | 0.508 | 14.46 | 0.435 | 1.09 | 324 |
| T = 9 WEEKS | 5-8° C. | 0.5 | 16.83 | 0.416 | 0.03 | 9 |
| | 20-25° C. | 0.51 | 15.41 | 0.431 | 0.206 | 62 |
| | 40° C. | 0.503 | 15.34 | 0.426 | 1.43 | 434 |
| T = 10 WEEKS | 5-8° C. | 0.506 | 16.36 | 0.423 | 0.04 | 12 |
| | 20-25° C. | 0.508 | 15.82 | 0.428 | 0.22 | 66 |
| | 40° C. | 0.507 | 15.2 | 0.430 | 1.67 | 501 |
| T = 12 WEEKS | 5-8° C. | 0.504 | 16.36 | 0.422 | 0.26 | 8 |
| | 20-25° C. | 0.501 | 15.82 | 0.422 | 1.8 | 55 |
| | 40° C. | 0.508 | 15.2 | 0.431 | 1.94 | 581 |

TABLE 10

Sample 6H

| TIME POINT | STORAGE CONDITIONS | Sample Weight (g) | Moisture Content (%) | Sample Dry Weight (g) | Fluoride Reading (ppm) | Fluoride Conc (ug/g) |
|---|---|---|---|---|---|---|
| T = 0 | 5-8° C. | 0.511 | 7.82 | 0.471 | 0.19 | 50 |
| | 20-25° C. | | | | | |
| | 40° C. | | | | | |
| T = 2 WEEKS | 5-8° C. | 0.510 | 7.07 | 0.474 | 0.17 | 46 |
| | 20-25° C. | 0.544 | 7.18 | 0.505 | 0.40 | 102 |
| | 40° C. | 0.502 | 8.16 | 0.461 | 1.10 | 308 |
| T = 4 WEEKS | 5-8° C. | 0.538 | 7.2 | 0.499 | 0.20 | 52 |
| | 20-25° C. | 0.508 | 6.21 | 0.476 | 0.38 | 103 |
| | 40° C. | 0.501 | 7.47 | 0.464 | 2.03 | 565 |
| T = 6 WEEKS | 5-8° C. | 0.509 | 6.38 | 0.477 | 0.16 | 44 |
| | 20-25° C. | 0.521 | 6.91 | 0.485 | 0.39 | 103 |
| | 40° C. | 0.500 | 7.08 | 0.465 | 2.04 | 566 |
| T = 8 WEEKS | 5-8° C. | 0.523 | 7.16 | 0.486 | 0.14 | 37 |
| | 20-25° C. | 0.530 | 7.31 | 0.491 | 0.31 | 81 |
| | 40° C. | 0.500 | 7.67 | 0.462 | 1.89 | 528 |
| T = 9 WEEKS | 5-8° C. | 0.531 | 7.89 | 0.489 | 0.35 | 92 |
| | 20-25° C. | 0.501 | 7.8 | 0.462 | 0.79 | 221 |
| | 40° C. | 0.518 | 8.19 | 0.476 | 2.41 | 654 |
| T = 10 WEEKS | 5-8° C. | 0.510 | 7.89 | 0.470 | 0.33 | 90 |
| | 20-25° C. | 0.516 | 7.80 | 0.476 | 0.88 | 239 |
| | 40° C. | 0.501 | 8.19 | 0.460 | 2.58 | 724 |
| T = 12 WEEKS | 5-8° C. | 0.504 | 7.89 | 0.464 | 2.03 | 57 |
| | 20-25° C. | 0.502 | 7.80 | 0.463 | 5.75 | 160 |
| | 40° C. | 0.495 | 8.19 | 0.454 | 3.20 | 908 |

TABLE 11

Example 6I

| TIME POINT | STORAGE CONDITIONS | Sample Weight (g) | Moisture Content (%) | Sample Dry Weight (g) | Fluoride Reading (ppm) | Fluoride Conc (ug/g) |
|---|---|---|---|---|---|---|
| T = 0 | 5-8° C. | 0.502 | 16.1 | 0.421 | <0.07 | <15 |
| | 20-25° C. | | | | | |
| | 40° C. | | | | | |
| T = 2 WEEKS | 5-8° C. | 0.520 | 16.9 | 0.432 | 0.03 | 9 |
| | 20-25° C. | 0.510 | 15.8 | 0.429 | 0.06 | 19 |
| | 40° C. | 0.510 | 14.5 | 0.436 | 0.70 | 214 |
| T = 4 WEEKS | 5-8° C. | 0.505 | 16.2 | 0.423 | 0.04 | 12 |
| | 20-25° C. | 0.519 | 14.7 | 0.443 | 0.03 | 9 |
| | 40° C. | 0.507 | 14.5 | 0.433 | 0.91 | 280 |
| T = 6 WEEKS | 5-8° C. | 0.513 | 16.8 | 0.427 | 0.02 | 7 |
| | 20-25° C. | 0.504 | 14.8 | 0.429 | 0.03 | 9 |
| | 40° C. | 0.554 | 14.1 | 0.476 | 1.09 | 305 |
| T = 8 WEEKS | 5-8° C. | 0.511 | 16.09 | 0.429 | 0.03 | 9 |
| | 20-25° C. | 0.505 | 15.58 | 0.426 | 0.03 | 9 |
| | 40° C. | 0.554 | 14.46 | 0.474 | 1.13 | 317 |
| T = 9 WEEKS | 5-8° C. | 0.506 | 16.69 | 0.422 | 0.04 | 12 |
| | 20-25° C. | 0.516 | 15.49 | 0.436 | 0.22 | 67 |
| | 40° C. | 0.526 | 15.07 | 0.447 | 1.75 | 522 |
| T = 10 WEEKS | 5-8° C. | 0.509 | 16.69 | 0.424 | 0.04 | 12 |
| | 20-25° C. | 0.505 | 15.49 | 0.427 | 0.23 | 72 |
| | 40° C. | 0.517 | 15.07 | 0.439 | 1.74 | 527 |
| T = 12 WEEKS | 5-8° C. | 0.503 | 16.69 | 0.419 | 0.314 | 9 |
| | 20-25° C. | 0.501 | 15.49 | 0.423 | 1.76 | 56 |
| | 40° C. | 0.517 | 15.07 | 0.439 | 2.22 | 674 |

TABLE 12

Sample 6J

| TIME POINT | STORAGE CONDITIONS | Sample Weight (g) | Moisture Content (%) | Sample Dry Weight (g) | Fluoride Reading (ppm) | Fluoride Conc (ug/g) |
|---|---|---|---|---|---|---|
| T = 0 | 5-8° C. | 0.563 | 8.59 | 0.515 | 0.13 | 33 |
| | 20-25° C. | | | | | |
| | 40° C. | | | | | |
| T = 2 WEEKS | 5-8° C. | 0.545 | 7.60 | 0.504 | 0.12 | 32 |
| | 20-25° C. | 0.520 | 7.35 | 0.482 | 0.25 | 69 |
| | 40° C. | 0.501 | 8.21 | 0.460 | 0.66 | 192 |
| T = 4 WEEKS | 5-8° C. | 0.513 | 7.22 | 0.476 | 0.11 | 31 |
| | 20-25° C. | 0.526 | 7.83 | 0.485 | 0.22 | 60 |
| | 40° C. | 0.516 | 7.83 | 0.476 | 0.91 | 254 |
| T = 6 WEEKS | 5-8° C. | 0.519 | 7.93 | 0.478 | 0.09 | 25 |
| | 20-25° C. | 0.503 | 8.00 | 0.463 | 0.21 | 60 |
| | 40° C. | 0.511 | 7.80 | 0.471 | 0.94 | 266 |
| T = 8 WEEKS | 5-8° C. | 0.518 | 8.16 | 0.476 | 0.11 | 31 |
| | 20-25° C. | 0.532 | 7.91 | 0.490 | 0.22 | 60 |
| | 40° C. | 0.509 | 8.11 | 0.468 | 0.97 | 276 |
| T = 9 WEEKS | 5-8° C. | 0.510 | 9.19 | 0.463 | 0.19 | 55 |
| | 20-25° C. | 0.535 | 8.44 | 0.490 | 0.62 | 168 |
| | 40° C. | 0.511 | 8.07 | 0.470 | 1.86 | 527 |
| T = 10 WEEKS | 5-8° C. | 0.503 | 9.19 | 0.457 | 0.18 | 52 |
| | 20-25° C. | 0.511 | 8.44 | 0.468 | 0.61 | 174 |
| | 40° C. | 0.509 | 8.07 | 0.468 | 1.87 | 533 |
| T = 12 WEEKS | 5-8° C. | 0.500 | 9.19 | 0.454 | 1.45 | 43 |
| | 20-25° C. | 0.510 | 8.44 | 0.467 | 4.57 | 130 |
| | 40° C. | 0.518 | 8.07 | 0.476 | 2.36 | 660 |

Example 7

Potassium Binding Capacity of Polyol Stabilized FAA

Materials. The materials used were potassium chloride (Reagent Plus grade, ≧99%, Sigma #P4504 or equivalent); de-ionized water greater than 18 megaöhm resistivity; IC potassium standard (1,000 ppm, Alltech Cat#37025 or equivalent); ion chromatography (IC) potassium standard, 1000 ppm from a secondary source (e.g. Fisher Scientific #CS-K2-2Y); and methanesulfonic acid (MSA, 99.5%; Aldrich #471356). The MSA was used to make the IC mobile phase if the apparatus used was unable to generate the mobile phase electrolytically.

Preparation of 200 mM KCl solution. Potassium chloride (14.91 g) was dissolved in 800 mL of water. A graduated cylinder was used and water was added to make a 1 L solution. This solution was the 200 mM potassium chloride solution for the binding assay.

QC and Linear Curve Preparation for IC Analysis. Potassium standard solutions (100, 250, 500 ppm) for IC were prepared by diluting a stock 1000 ppm solution with distilled (DI) water. The QC check standard was obtained by diluting a second source certified 1000 ppm potassium standard with DI water to achieve 250 ppm concentration.

Preparation of Sample Solution. Two samples of Ca(polyFAA) prepared by the method of Example 4 (500 mg) were placed into separate screw top vials. Using the equation below, the amount of 200 mM KCl solution to add to the vial was calculated:

$$\frac{\frac{M}{100} \times \left[100 - S \times \left(1 - \frac{W}{100}\right) - W\right]}{20} (mL) \quad i.$$

where M is Ca(polyFAA) sample weight (mg), S is sorbitol content based on dry weight of Ca(polyFAA), and W is loss on drying (%). The calculated volume of 200 mM KCl solution was added to each vial using a 10 mL pipettor. The vials were capped tightly. Two blank vials containing 15 mL of 200 mM KCl solution were prepared. The vials were tumbled on a rotary tumbler for two hours at about 35 rpm. After two hours, the vials were removed from the tumbler. The contents were allowed to settle for 5 minutes. Each sample (2-10 mL) and a blank were filtered over a 0.45 micron filter. Each filtered sample was diluted 1:20 by adding 500 µL of each sample or blank to 9500 µL of water. The diluted filtrate was analyzed for potassium content using IC.

Sample Analysis by IC. If a 20 mM MSA mobile phase could not be generated electrolytically, the 20 mM stock MSA mobile phase was made by diluting MSA in water. The IC had the following settings: injection volume: 5 µL; flow rate: 1 mL/min; column temperature: 35° C.; sample compartment temperature: ambient; run time: 20 min; and CD25 settings: current 88 mA, cell temperature 35° C., autorange. Each blank and sample was injected twice.

The IC system used was a Dionex IC System 2000 equipped with AS50 autosampler, conductivity Detector CD25 and DS3 flow cell. The column used was a CS12A 250×4 mm ID analytical column, Dionex #016181 coupled with a CG12A 50×4 mm ID guard column (optional), Dionex#046074. The suppressor used was a Dionex CSRS-Ultra II (4 mm) Suppressor, Dionex#061563. The software used for data acquisition was Dionex Chromeleon Chromatography Software. The eluent cartridge was a Dionex #058902 to generate the methanesulfonic acid (MSA) mobile phase electrolytically.

Data Analysis. The concentration of potassium was reported in mM. The equation below was used to calculate the binding capacity of each sample:

Binding capacity (mmol/g)=$(c_{Blank} - c_{Sample})$ where $c_{Blank}$ is average concentration of potassium in the 20-fold diluted blank by IC analysis (mM), and $c_{sample}$ is average concentration of potassium in the 20-fold diluted sample solution by IC analysis (mM). The average of the duplicates was reported. The deviation of each individual value was a maximum of 10% from the mean. When a larger deviation was obtained, the assay was repeated.

Results. A Ca(polyFAA) sample prepared by the process described in Example 4 had a potassium binding capacity of 1.60 mmol/g. A similar Ca(polyFAA) sample was slurried with a 20 wt. %, 25 wt. %, 30 wt. %, and a 45 wt. % solution of D-sorbitol using the process described in Example 6. The potassium binding capacities for those stabilized Ca(polyFAA) samples are described in the Table 13.

TABLE 13

| Ca(polyFAA) slurried with | Potassium Binding Capacity (mmol/g) |
| --- | --- |
| 20 wt. % sorbitol | 1.62 |
| 25 wt. % sorbitol | 1.67 |
| 30 wt. % sorbitol | 1.61 |
| 45 wt. % sorbitol | 1.63 |

Example 8

Human Clinical Study

Part A:

Methyl 2-fluoroacrylate (MeFA) was purchased and was vacuum distilled before use. Divinylbenzene (DVB) was purchased from Aldrich, technical grade, 80%, mixture of isomers, and was used as received. 1,7-octadiene (ODE), lauroyl peroxide (LPO), polyvinyl alcohol (PVA) (typical molecular weight 85,000-146,000, 87-89% hydrolyzed), sodium chloride (NaCl), sodium phosphate dibasic heptahydrate ($Na_2HPO_4 \cdot 7H_2O$) and sodium phosphate monobasic monohydrate ($NaH_2PO_4 \cdot H_2O$) were purchased from commercial sources and used as received.

In an appropriately sized reactor with appropriate stirring and other equipment, a 90:5:5 weight ratio mixture of organic phase of monomers was prepared by mixing methyl 2-fluoroacrylate, 1,7-octadiene, and divinylbenzene. One-half part of lauroyl peroxide was added as an initiator of the polymerization reaction. A stabilizing aqueous phase was prepared from water, polyvinyl alcohol, phosphates, sodium chloride, and sodium nitrite. The aqueous and monomer phases were mixed together under nitrogen at atmospheric pressure, while maintaining the temperature below 30° C. The reaction mixture was gradually heated while stirring continuously. Once the polymerization reaction has started, the temperature of the reaction mixture was allowed to rise to a maximum of 95° C.

After completion of the polymerization reaction, the reaction mixture was cooled and the aqueous phase was removed. Water was added, the mixture was stirred, and the solid material was isolated by filtration. The solid was then washed with water to yield a crosslinked (methyl 2-fluoroacrylate)-divinylbenzene-1,7-octadiene polymer. The (methyl 2-fluoroacrylate)-divinylbenzene-1,7-octadiene copolymer was hydrolyzed with an excess of aqueous sodium hydroxide solution at 90° C. for 24 hours to yield (sodium 2-fluoroacrylate)-divinylbenzene-1,7-octadiene polymer. After hydrolysis, the solid was filtered and washed with water. The (sodium 2-fluoroacrylate)-divinylbenzene-1,7-octadiene polymer was exposed at room temperature to an excess of aqueous calcium chloride solution to yield insoluble cross-linked (calcium 2-fluoroacrylate)-divinylbenzene-1,7-octadiene polymer.

After the calcium ion exchange, the wet polymer is slurried with 25-30% w/w aqueous solution of sorbitol at ambient temperature to yield sorbitol-loaded polymer. Excess sorbitol is removed by filtration. The resulting polymer is dried at 20-30° C. until the desired moisture content (10-25 w/w/%) is reached. This provides a sorbitol loaded, cross-linked (calcium 2-fluoroacrylate)-divinylbenzene-1,7-octadiene polymer.

Part B:

The objective of the study was to evaluate the equivalence of once a day, two times a day and three times a day dosing of the polymer from Part A of this example. After a four day period to control diet, 12 healthy volunteers were randomized in an open-label, multiple-dose crossover study. The polymer was administered orally as an aqueous suspension of 30 grams (g) once a day for six days, 15 g twice a day for six days, and 10 g three times a day for 6 days in a randomly assigned order based upon 1 of 6 dosing sequences. Laboratory and adverse event assessments were performed throughout the study to monitor safety and tolerability. Subjects were required to consume a controlled diet for the duration of the study. Feces and urine were collected over 24 hour intervals on certain study days to assess potassium excretion.

Subjects were healthy adult males or females without a history of significant medical disease, 18 to 55 years of age, with a body mass index between 19 and 29 kg/m$^2$ at the screening visit, serum potassium level >4.0 and ≦5.0 mEq/L, and serum magnesium, calcium, and sodium levels within normal range. Females of childbearing potential must have been non-pregnant and non-lactating and must have used a highly effective form of contraception before, during, and after the study.

Multiple-dose administration of 30 g polymer for 6 days each as either 30 g once daily, 15 g twice daily or 10 g three-times daily, respectively was well tolerated. No serious adverse events were reported, and all adverse events were mild or moderate in severity. An effect was apparent for fecal and urinary excretion of potassium.

For fecal potassium excretion, the mean daily values and change from baseline values were significantly increased for all three dosing regimens. The volunteers receiving the polymer once per day excreted 82.8% of the amount of fecal potassium as those volunteers who received substantially the same amount of the same polymer three-times per day. It is also shown that volunteers receiving the polymer twice per day excreted 91.5% of the amount of fecal potassium as those volunteers who received substantially the same amount of the same polymer three-times per day. For urinary potassium excretion, the mean daily values and change from baseline values were significantly decreased for all three dosing regimens. Surprisingly, there was no statistically significant difference between the three dosing regimens.

Regarding tolerability, 2 of the 12 subjects receiving once a day dosing or twice a day dosing reported mild or moderate gastrointestinal adverse events (including flatulence, diarrhea, abdominal pain, constipation, stomatitis, nausea and/or vomiting). Also, 2 of 12 subjects reported mild or moderate gastrointestinal adverse events on the baseline control diet. Thus, less than 16.7% of these subjects reported mild or moderate gastrointestinal adverse events, an indication that, as used herein, dosing once or twice a day was well tolerated. None of the subjects reported severe gastrointestinal adverse events for any of the dosing regimens or at baseline.

Part C:

Another study was performed to assess the safety and efficacy of a binding polymer that was the same as described above in Part A of this example, but without the sorbitol loading. Thirty-three healthy subjects (26 male and 7 female) between the ages of 18 and 55 years received single and multiple doses of polymer or placebo in a double-blind, randomized, parallel-group study. Eight subjects each were randomly assigned to one of four treatment groups receiving polymer or matching placebo. The subjects received 1, 5, 10, or 20 g of polymer or placebo as a single dose on study day 1, followed by three times daily dosing for eight days following seven days of diet control. Subjects were required to consume a controlled diet for the duration of the study.

The polymer was well-tolerated by all subjects. No serious adverse events occurred. Gastrointestinal adverse events reported were mild to moderate in severity for one subject. There was no apparent dose response relationship in gastrointestinal or overall adverse event reporting, and no increase in adverse event reports versus placebo.

At the end of the multiple-dose study period, a dose response effect was apparent for fecal and urinary excretion of potassium. For fecal potassium excretion, the mean daily values and change from baseline values were significantly increased in a dose-related manner. For urinary potassium excretion, the mean daily values and change from baseline values were decreased in a dose-related manner.

In comparison of Part C to Part B, those volunteers receiving the same amount of polymer that had the sorbitol loading (Part B) excreted about 20% more potassium in the feces as compared to those volunteers receiving the non-sorbitol loaded polymer (Part C).

When introducing elements of the present invention or the embodiments(s) thereof, the articles "a", "an", "the" and "said" are intended to mean that there are one or more of the elements. The terms "comprising", "including" and "having" are intended to be inclusive and mean that there may be additional elements other than the listed elements.

In view of the above, it will be seen that the several objects of the invention are achieved and other advantageous results attained.

As various changes could be made in the above compositions and methods without departing from the scope of the invention, it is intended that all matter contained in the above description shall be interpreted as illustrative and not in a limiting sense.

What is claimed is:

1. A pharmaceutical composition comprising a crosslinked cation exchange polymer salt loaded with a stabilizing amount of a linear sugar alcohol by slurrying in a solution the linear sugar alcohol with the crosslinked cation exchange polymer salt, wherein the stabilizing amount of the linear sugar alcohol is from about 10 wt. % to about 35 wt. % based on the total weight of the composition, and the crosslinked cation exchange polymer salt comprising structural units of Formulae 1 and 2, Formulae 1 and 3, or Formulae 1, 2, and 3, wherein Formula 1, Formula 2, and Formula 3 have the following structures:

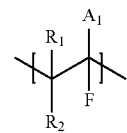

Formula 1

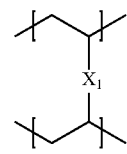

Formula 2

-continued

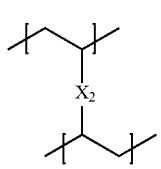
Formula 3 wherein
R₁ and R₂ are each independently hydrogen, alkyl, cycloalkyl, or aryl;
A₁ is carboxylic, phosphonic, or phosphoric;
X₁ is arylene; and
X₂ is alkylene, an ether moiety, or an amide moiety; and
either the structural unit of Formula 1 constituting at least about 80 wt. % based on the total weight of the structural units of Formulae 1 and 2, Formulae 1 and 3, or Formulae 1, 2, and 3 in the polymer salt, or the mole fraction of the structural unit of Formula 1 in the polymer salt being at least about 0.87 based on the total number of moles of the structural units of Formulae 1 and 2, Formulae 1 and 3, or Formulae 1, 2, and 3 in the polymer salt.

2. A pharmaceutical composition comprising a crosslinked cation exchange polymer salt and a linear sugar alcohol, wherein the cation exchange polymer salt is loaded with the linear sugar alcohol by slurrying in a solution the linear sugar alcohol with the crosslinked cation exchange polymer salt, the crosslinked cation exchange polymer salt comprising structural units of Formulae 1 and 2, Formulae 1 and 3, or Formulae 1, 2, and 3, wherein Formula 1, Formula 2, and Formula 3 have the following structures:

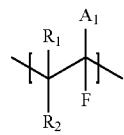
Formula 1

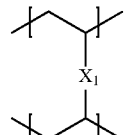
Formula 2

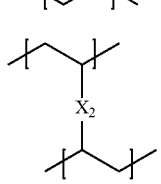
Formula 3 wherein
R₁ and R₂ are each independently hydrogen, alkyl, cycloalkyl, or aryl;
A₁ is carboxylic, phosphonic, or phosphoric;
X₁ is arylene; and
X₂ is alkylene, an ether moiety, or an amide moiety; and
either the structural unit of Formula 1 constituting at least about 80 wt. % based on the total weight of the structural units of Formulae 1 and 2, Formulae 1 and 3, or Formulae 1, 2, and 3 in the polymer salt, or the mole fraction of the structural unit of Formula 1 in the polymer salt being at least about 0.87 based on the total number of moles of the structural units of Formulae 1 and 2, Formulae 1 and 3, or Formulae 1, 2, and 3 in the polymer salt; and the polymer salt is loaded with the linear sugar alcohol in an amount sufficient to reduce the release of fluoride ion from the cation exchange polymer salt upon storage as compared to an otherwise identical composition containing no linear sugar alcohol at the same temperature and storage time, and wherein there is no more than 1000 ppm of inorganic fluoride in the composition after storage.

3. The pharmaceutical composition of claim 1 wherein the structural units of Formulae 1, 2, and 3 have the following structures:

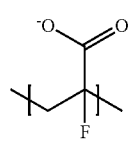
Formula 1A

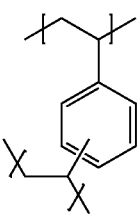
Formula 2A

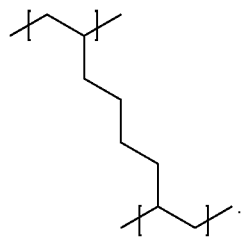
Formula 3A

4. The pharmaceutical composition of claim 1 wherein the polymer salt comprises structural units of Formulae 1, 2 and 3.

5. The pharmaceutical composition of claim 1 wherein the polymer salt comprises structural units of Formulae 1 and 2.

6. The pharmaceutical composition of claim 1 wherein the polymer salt comprises structural units of Formulae 1 and 3.

7. A pharmaceutical composition comprising a crosslinked cation exchange polymer salt and from about 10 wt. % to about 35 wt. % of a linear sugar alcohol based on the total weight of the composition, wherein a crosslinked cation exchange polymer is a reaction product of a polymerization mixture comprising monomers of either (i) Formulae 11 and 22, (ii) Formulae 11 and 33, or (iii) Formulae 11, 22, and 33, the crosslinked cation exchange polymer is converted to the crosslinked cation exchange polymer salt, and the crosslinked cation exchange polymer salt is slurried in a solution of the linear sugar alcohol, wherein Formula 11, Formula 22, and Formula 33 have the following structures:

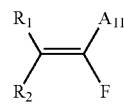
Formula 11

-continued

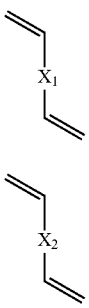

Formula 22

Formula 33 wherein

R₁ and R₂ are each independently hydrogen, alkyl, cycloalkyl, or aryl;

$A_{11}$ is an optionally protected carboxylic, phosphonic, or phosphoric;

$X_1$ is arylene; and $X_2$ is alkylene, an ether moiety, or an amide moiety; and either the monomer of Formula 11 constituting at least about 80 wt. % based on the total weight of the monomers of Formulae 11 and 22, Formulae 11 and 33, or Formulae 11, 22, and 33 in the polymerization mixture, or the mole fraction of the monomer of Formula 11 in the polymer salt being at least about 0.87 based on the total number of moles of the monomers of Formulae 11 and 22, Formulae 11 and 33, or Formulae 11, 22, and 33 in the polymerization mixture.

8. A pharmaceutical composition comprising a crosslinked cation exchange polymer salt and a linear sugar alcohol, wherein a crosslinked cation exchange polymer is a reaction product of a polymerization mixture comprising monomers of either (i) Formulae 11 and 22, (ii) Formulae 11 and 33, or (iii) Formulae 11, 22, and 33, the crosslinked cation exchange polymer is converted to the crosslinked cation exchange polymer salt, and the crosslinked cation exchange polymer salt is slurried in a solution of the linear sugar alcohol;

the linear sugar alcohol is in an amount sufficient to reduce the release of fluoride ion from the polymer salt upon storage as compared to an otherwise identical composition containing no linear sugar alcohol at the same temperature and storage time, and wherein there is no more than 1000 ppm of inorganic fluoride in the composition after storage, and Formula 11, Formula 22, and Formula 33 have the following structures:

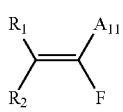

Formula 11

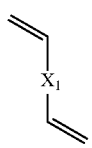

Formula 22

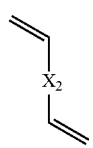

Formula 33 wherein

R₁ and R₂ are each independently hydrogen, alkyl, cycloalkyl, or aryl;

$A_{11}$ is an optionally protected carboxylic, phosphonic, or phosphoric;

$X_1$ is arylene; and $X_2$ is alkylene, an ether moiety, or an amide moiety; and either the monomer of Formula 11 constituting at least about 80 wt. % based on the total weight of the monomers of Formulae 11 and 22, Formulae 11 and 33, or Formulae 11, 22, and 33 in the polymerization mixture, or the mole fraction of the monomer of Formula 11 in the polymer salt being at least about 0.87 based on the total number of moles of the monomers of Formulae 11 and 22, Formulae 11 and 33, or Formulae 11, 22, and 33 in the polymerization mixture.

9. The pharmaceutical composition of claim 7 wherein Formulae 11, 22, and 33 have the following structures:

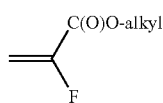

Formula 11A

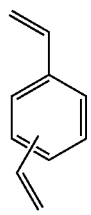

Formula 22A

Formula 33A

10. The pharmaceutical composition of claim 7 wherein the polymer comprises structural units of Formulae 11, 22, and 33.

11. The pharmaceutical composition of claim 7 wherein the polymer comprises structural units of Formulae 11 and 22.

12. The pharmaceutical composition of claim 7 wherein the polymer comprises structural units of Formulae 11 and 33.

13. The pharmaceutical composition of claim 1 wherein the salt comprises calcium, sodium, or a combination thereof.

14. The pharmaceutical composition of claim 1 wherein the linear sugar alcohol is selected from the group consisting of arabitol, erythritol, glycerol, maltitol, mannitol, ribitol, sorbitol, xylitol, threitol, galactitol, isomalt, iditol, lactitol and combinations thereof.

15. The pharmaceutical composition of claim 1 wherein the linear sugar alcohol is sorbitol, xylitol, or a combination thereof.

16. The pharmaceutical composition of claim 1 further comprising from 10 wt. % to 25 wt. % moisture or water based on the total weight of the linear sugar alcohol, polymer and moisture or water.

17. The pharmaceutical composition of claim 2 wherein the concentration of inorganic fluoride is less than about 1000 ppm after storage at about 40° C. for about 6 weeks.

18. The pharmaceutical composition of claim 2 wherein the concentration of inorganic fluoride is less than about 500 ppm after storage at about 25° C. for about 6 weeks.

19. A method for removing potassium from the gastrointestinal tract of an animal subject in need thereof, the method comprising administering the pharmaceutical composition of claim 1 to the subject, whereby the pharmaceutical composition passes through the gastrointestinal tract of the subject, and removes a therapeutically effective amount of potassium ion from the gastrointestinal tract of the subject.

20. A method for removing potassium from the gastrointestinal tract of an animal subject, the method comprising administering once per day to the subject the pharmaceutical composition of claim 1, wherein a daily amount of the polymer salt has a potassium binding capacity of at least 75% of the same daily amount of the same polymer salt administered three times per day.

21. A method of removing potassium from the gastrointestinal tract of an animal subject in need thereof, the method comprising administering once per day to the subject an effective amount of the pharmaceutical composition of claim 1.

22. A method of removing potassium from the gastrointestinal tract of an animal subject in need thereof, the method comprising administering the pharmaceutical composition of claim 7 to the subject, whereby the pharmaceutical composition passes through the gastrointestinal tract of the subject, and removes a therapeutically effective amount of potassium ion from the gastrointestinal tract of the subject.

23. A method for removing potassium from the gastrointestinal tract of an animal subject in need thereof, the method comprising administering an effective amount of the pharmaceutical composition of claim 1, which extracts about 5% more potassium as compared to the same dose and same administration frequency of the same polymer salt without stabilization by a linear sugar alcohol.

24. The pharmaceutical composition of claim 1 wherein the salt comprises calcium.

25. The pharmaceutical composition of claim 1 wherein the linear sugar alcohol comprises sorbitol.

26. The pharmaceutical composition of claim 1 wherein the linear sugar alcohol comprises sorbitol and the salt comprises calcium.

27. The pharmaceutical composition of claim 26 further comprising from 10 wt. % to 25 wt. % moisture or water based on the total weight of the linear sugar alcohol, polymer salt and moisture or water.

28. The pharmaceutical composition of claim 27 wherein the polymer salt comprises structural units of Formulae 1, 2 and 3 of the following structures:

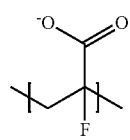

Formula 1A

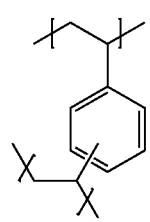

Formula 2A

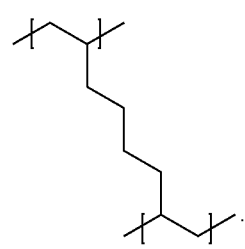

Formula 3A

29. The pharmaceutical composition of claim 28 wherein the polymer salt comprises structural units of Formulae 1A, 2A, and 3A and either:

(i) the structural units of Formula 1A constitute at least about 85 wt. % based on the total weight of structural units of Formulae 1A, 2A, and 3A in the polymer salt calculated from the amounts of monomers used in the polymerization reaction, and the weight ratio of the structural unit of Formula 2A to the structural unit of Formula 3A is from about 4:1 to about 1:4, or (ii) the mole fraction of the structural unit of Formula 1A in the polymer salt is at least about 0.87 based on the total number of moles of the structural units of Formulae 1A, 2A, and 3A calculated from the amounts of monomers used in the polymerization reaction, and the mole ratio of the structural unit of Formula 2A to the structural unit of Formula 3A is from about 0.2:1 to about 7:1.

30. The pharmaceutical composition of claim 2 further comprising from 10 wt. % to 25 wt. % moisture or water based on the total weight of the linear sugar alcohol, polymer salt and moisture or water.

31. The pharmaceutical composition of claim 2 wherein the salt comprises calcium, the linear sugar alcohol comprises sorbitol, and the structural units of Formulae 1, 2, and 3 have the following structures:

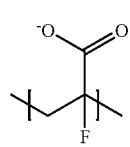

Formula 1A

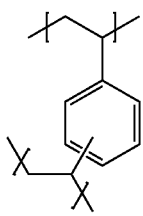

Formula 2A

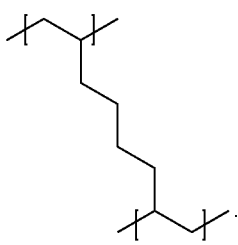

Formula 3A

32. The pharmaceutical composition of claim 31 further comprising from 10 wt. % to 25 wt. % moisture or water based on the total weight of the linear sugar alcohol, polymer salt and moisture or water.

33. The pharmaceutical composition of claim 32 wherein the polymer salt comprises structural units of Formulae 1A, 2A and 3A and either:
(i) the structural units of Formula 1A constitute at least about 85 wt. % based on the total weight of structural units of Formulae 1A, 2A, and 3A in the polymer salt calculated from the amounts of monomers used in the polymerization reaction, and the weight ratio of the structural unit of Formula 2A to the structural unit of Formula 3A is from about 4:1 to about 1:4, or
(ii) the mole fraction of the structural unit of Formula 1A in the polymer salt is at least about 0.87 based on the total number of moles of the structural units of Formulae 1A, 2A, and 3A calculated from the amounts of monomers used in the polymerization reaction, and the mole ratio of the structural unit of Formula 2A to the structural unit of Formula 3A is from about 0.2:1 to about 7:1.

34. The pharmaceutical composition of claim 7 further comprising from 10 wt. % to 25 wt. % moisture or water based on the total weight of the linear sugar alcohol, polymer salt and moisture or water.

35. The pharmaceutical composition of claim 7 wherein the salt comprises calcium.

36. The pharmaceutical composition of claim 7 wherein the linear sugar alcohol comprises sorbitol.

37. The pharmaceutical composition of claim 7 wherein the linear sugar alcohol comprises sorbitol and the salt comprises calcium.

38. The pharmaceutical composition of claim 37 further comprising from 10 wt. % to 25 wt. % moisture or water based on the total weight of the linear sugar alcohol, polymer salt and moisture or water.

39. The pharmaceutical composition of claim 38 wherein the polymer salt comprises the monomers of Formulae 11, 22, and 33 of the following structures:

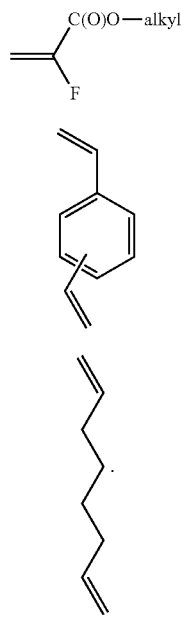

Formula 11A

Formula 22A

Formula 33A

40. The pharmaceutical composition of claim 39 wherein the polymer salt comprises the monomers of Formulae 11A, 22A, and 33A and either:
(i) the monomers of Formula 11A constitute at least about 85 wt. % based on the total weight of monomers of Formulae 11A, 22A, and 33A in the polymerization mixture and the weight ratio of monomers of Formula 22A to monomers of Formula 33A is from about 4:1 to about 1:4, or
(ii) the mole fraction of the monomer of Formula 11A in the polymerization mixture is at least about 0.87 based on the total number of moles of the monomers of Formulae 11A, 22A, and 33A and the mole ratio of the monomer of Formula 22A to the monomer of Formula 33A in the polymerization mixture is from about 0.2:1 to about 7:1.

41. The pharmaceutical composition of claim 8 further comprising from 10 wt. % to 25 wt. % moisture or water based on the total weight of the linear sugar alcohol, polymer salt and moisture or water.

42. The pharmaceutical composition of claim 8 wherein the salt comprises calcium, the linear sugar alcohol comprises sorbitol, and the polymer comprises the monomers of Formulae 11, 22, and 33 of the following structures:

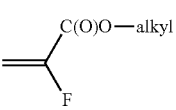

Formula 11A

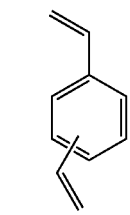

Formula 22A

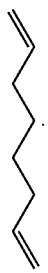

Formula 33A

43. The pharmaceutical composition of claim 42 further comprising from 10 wt. % to 25 wt. % moisture or water based on the total weight of the linear sugar alcohol, polymer salt and moisture or water.

44. The pharmaceutical composition of claim 43 wherein the polymer salt comprises the monomers of Formulae 11A, 22A and 33A and either:
  (i) the monomers of Formula 11A constitute at least about 85 wt. % based on the total weight of monomers of Formulae 11A, 22A, and 33A in the polymerization mixture and the weight ratio of monomers of Formula 22A to monomers of Formula 33A is from about 4:1 to about 1:4, or
  (ii) the mole fraction of the monomer of Formula 11A in the polymerization mixture is at least about 0.87 based on the total number of moles of the monomers of Formulae 11A, 22A, and 33A and the mole ratio of the monomer of Formula 22A to the monomer of Formula 33A in the polymerization mixture is from about 0.2:1 to about 7:1.

45. The pharmaceutical composition of claim 2 wherein the salt comprises calcium, sodium, or a combination thereof.

46. The pharmaceutical composition of claim 2 wherein the salt comprises calcium.

47. The pharmaceutical composition of claim 2 wherein the linear sugar alcohol is selected from the group consisting of arabitol, erythritol, glycerol, maltitol, mannitol, ribitol, sorbitol, xylitol, threitol, galactitol, isomalt, iditol, lactitol and combinations thereof.

48. The pharmaceutical composition of claim 47 wherein the linear sugar alcohol is sorbitol, xylitol, or a combination thereof.

49. The pharmaceutical composition of claim 2 wherein the linear sugar alcohol comprises sorbitol.

50. The pharmaceutical composition of claim 2 wherein the linear sugar alcohol comprises sorbitol and the salt comprises calcium.

51. The pharmaceutical composition of claim 2 wherein the structural units of Formulae 1, 2, and 3 have the following structures:

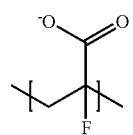

Formula 1A

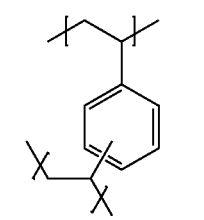

Formula 2A

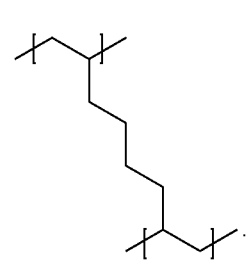

Formula 3A

52. The pharmaceutical composition of claim 7 wherein the crosslinked cation exchange polymer salt is in bead form.

53. The pharmaceutical composition of claim 7 wherein the salt comprises calcium, sodium, or a combination thereof.

54. The pharmaceutical composition of claim 8 wherein the salt comprises calcium.

55. The pharmaceutical composition of claim 7 wherein the linear sugar alcohol is selected from the group consisting of arabitol, erythritol, glycerol, maltitol, mannitol, ribitol, sorbitol, xylitol, threitol, galactitol, isomalt, iditol, lactitol and combinations thereof.

56. The pharmaceutical composition of claim 55 wherein the linear sugar alcohol is sorbitol, xylitol, or a combination thereof.

57. The pharmaceutical composition of claim 8 wherein the linear sugar alcohol comprises sorbitol.

58. The pharmaceutical composition of claim 8 wherein the linear sugar alcohol comprises sorbitol and the salt comprises calcium.

59. The pharmaceutical composition of claim 8 comprising the monomers of Formulae 11A, 22A, and 33A having the following structures:

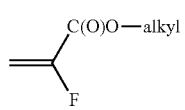

Formula 11A

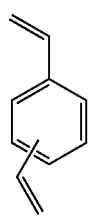

Formula 22A

Formula 33A

60. The pharmaceutical composition of claim 8 wherein the crosslinked cation exchange polymer salt is in bead form.

61. A pharmaceutical composition comprising a crosslinked cation exchange polymer salt in bead form having a stabilizing amount of a linear sugar alcohol loaded onto the polymer salt by slurrying in a solution the linear sugar alcohol with the crosslinked cation exchange polymer salt, wherein the stabilizing amount of the linear sugar alcohol is from about 10 wt. % to about 35 wt. % based on the total weight of the composition, the crosslinked cation exchange polymer salt comprising structural units of Formulae 1 and 2, Formulae 1 and 3, or Formulae 1, 2, and 3, wherein Formula 1, Formula 2, and Formula 3 have the following structures:

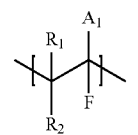

Formula 1

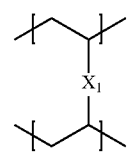

Formula 2

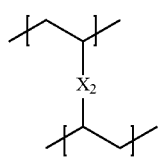

Formula 3 wherein
R$_1$ and R$_2$ are each independently hydrogen, alkyl, cycloalkyl, or aryl;
A$_1$ is carboxylic, phosphonic, or phosphoric;
X$_1$ is arylene; and
X$_2$ is alkylene, an ether moiety, or an amide moiety; and
either the structural unit of Formula 1 constituting at least about 80 wt. % based on the total weight of the structural units of Formulae 1 and 2, Formulae 1 and 3, or Formulae 1, 2, and 3 in the polymer salt, or the mole fraction of the structural unit of Formula 1 in the polymer salt being at least about 0.87 based on the total number of moles of the structural units of Formulae 1 and 2, Formulae 1 and 3, or Formulae 1, 2, and 3 in the polymer salt.

62. The pharmaceutical composition of claim 61 further comprising from 10 wt. % to 25 wt. % moisture or water based on the total weight of the linear sugar alcohol, polymer salt and moisture or water.

63. The pharmaceutical composition of claim 61 wherein the salt comprises calcium.

64. The pharmaceutical composition of claim 61 wherein the linear sugar alcohol comprises sorbitol.

65. The pharmaceutical composition of claim 61 wherein the linear sugar alcohol comprises sorbitol and the salt comprises calcium.

66. The pharmaceutical composition of claim 65 wherein the structural units of Formulae 1, 2, and 3 have the following structures:

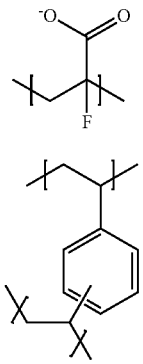

Formula 1A

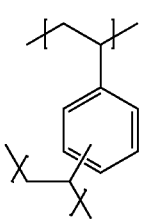

Formula 2A

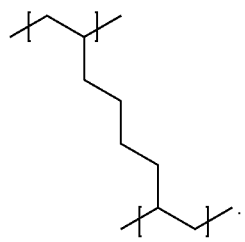

Formula 3A

67. The pharmaceutical composition of claim 66 further comprising from 10 wt. % to 25 wt. % moisture or water based on the total weight of the linear sugar alcohol, polymer salt and moisture or water.

68. The pharmaceutical composition of claim 67 wherein the polymer salt comprises structural units of Formulae 1A, 2A and 3A and either:
(i) the structural units of Formula 1A constitute at least about 85 wt. % based on the total weight of structural units of Formulae 1A, 2A, and 3A in the polymer salt calculated from the amounts of monomers used in the polymerization reaction, and the weight ratio of the structural unit of Formula 2A to the structural unit of Formula 3A is from about 4:1 to about 1:4, or
(ii) the mole fraction of the structural unit of Formula 1A in the polymer salt is at least about 0.87 based on the total number of moles of the structural units of Formulae 1A, 2A, and 3A calculated from the amounts of monomers used in the polymerization reaction, and the mole ratio of the structural unit of Formula 2A to the structural unit of Formula 3A is from about 0.2:1 to about 7:1.

69. A pharmaceutical composition comprising a crosslinked cation exchange polymer salt in bead form having a linear sugar alcohol loaded onto the polymer salt by slurrying in a solution the linear sugar alcohol with the crosslinked cation exchange polymer salt, the crosslinked cation exchange polymer comprising structural units of Formulae 1 and 2, Formulae 1 and 3, or Formulae 1, 2, and 3, wherein Formula 1, Formula 2, and Formula 3 have the following structures:

Formula 1

Formula 2

Formula 3 wherein
R$_1$ and R$_2$ are each independently hydrogen, alkyl, cycloalkyl, or aryl;
A$_1$ is carboxylic, phosphonic, or phosphoric;
X$_1$ is arylene; and
X$_2$ is alkylene, an ether moiety, or an amide moiety; and
either the structural unit of Formula 1 constituting at least about 80 wt. % based on the total weight of the structural units of Formulae 1 and 2, Formulae 1 and 3, or Formulae 1, 2, and 3 in the polymer salt, or the mole fraction of the structural unit of Formula 1 in the polymer salt being at least about 0.87 based on the total number of moles of the structural units of Formulae 1 and 2, Formulae 1 and 3, or Formulae 1, 2, and 3 in the polymer salt; and
the polymer salt is loaded with the linear sugar alcohol in an amount sufficient to reduce the release of fluoride ion from the cation exchange polymer salt upon storage as compared to an otherwise identical composition containing no linear sugar alcohol at the same temperature and storage time, and wherein there is no more than 1000 ppm of inorganic fluoride in the composition after storage.

70. The pharmaceutical composition of claim 69 further comprising from 10 wt. % to 25 wt. % moisture or water based on the total weight of the linear sugar alcohol, polymer salt and moisture or water.

71. The pharmaceutical composition of claim 69 wherein the salt comprises calcium.

72. The pharmaceutical composition of claim 69 wherein the linear sugar alcohol comprises sorbitol.

73. The pharmaceutical composition of claim 69 wherein the linear sugar alcohol comprises sorbitol and the salt comprises calcium.

74. The pharmaceutical composition of claim 73 wherein the structural units of Formulae 1, 2, and 3 have the following structures:

Formula 1A

Formula 2A

Formula 3A

75. The pharmaceutical composition of claim 74 further comprising from 10 wt. % to 25 wt. % moisture or water based on the total weight of the linear sugar alcohol, polymer salt and moisture or water.

76. The pharmaceutical composition of claim 75 wherein the polymer salt comprises structural units of Formulae 1A, 2A and 3A and either:
(i) the structural units of Formula 1A constitute at least about 85 wt. % based on the total weight of structural units of Formulae 1A, 2A, and 3A in the polymer salt calculated from the amounts of monomers used in the polymerization reaction, and the weight ratio of the structural unit of Formula 2A to the structural unit of Formula 3A is from about 4:1 to about 1:4, or
(ii) the mole fraction of the structural unit of Formula 1A in the polymer salt is at least about 0.87 based on the total number of moles of the structural units of Formulae 1A, 2A, and 3A calculated from the amounts of monomers used in the polymerization reaction, and the mole ratio of the structural unit of Formula 2A to the structural unit of Formula 3A is from about 0.2:1 to about 7:1.

77. The method of claim 19 wherein the pharmaceutical composition is administered once per day.

78. The method of claim 19 wherein the pharmaceutical composition is administered twice per day.

* * * * *

UNITED STATES PATENT AND TRADEMARK OFFICE
CERTIFICATE OF CORRECTION

| | | |
|---|---|---|
| PATENT NO. | : 8,337,824 B2 | Page 1 of 1 |
| APPLICATION NO. | : 12/545810 | |
| DATED | : December 25, 2012 | |
| INVENTOR(S) | : Albrecht et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 280 days.

Signed and Sealed this
Fifth Day of November, 2013

Teresa Stanek Rea
*Deputy Director of the United States Patent and Trademark Office*